United States Patent [19]

Klioze

[11] Patent Number: 4,544,745

[45] Date of Patent: Oct. 1, 1985

[54] CIS-4A-ARYL, 1, 2, 3, 4, 4A, 9B-HEXAHYDRO-BENZOFURO-[3,2-C]-PYRIDINES USEFUL AS ANALGESICS

[75] Inventor: Solomon S. Klioze, Flemington, N.J.

[73] Assignee: Hoechst-Roussel Pharmaceuticals Inc., Somerville, N.J.

[21] Appl. No.: 685,261

[22] Filed: Dec. 21, 1984

Related U.S. Application Data

[62] Division of Ser. No. 400,576, Jul. 22, 1982, Pat. No. 4,507,306.

[51] Int. Cl.$^4$ ......................................... C07D 491/048
[52] U.S. Cl. ..................................................... 546/89
[58] Field of Search ......................................... 546/89

[56] References Cited

FOREIGN PATENT DOCUMENTS 51-23519  7/1976  Japan ..................................... 546/89

OTHER PUBLICATIONS

*Synthesis of Benzofuro[3,2-e][1,4]Diazepine,* Settimj et al., Chem. Abstracts 100:103303p.

Primary Examiner—Henry R. Jiles
Assistant Examiner—P. Ann Bucci
Attorney, Agent, or Firm—Tatsuya Ikeda; Jerome Rosenstock

[57] ABSTRACT

Cis-4a-aryl, 1, 2, 3, 4, 4A, 9B-hexahydro-benzofuro-[3,2-C]- pyridines, useful as analgesic and anticonvulsant agents are described.

16 Claims, No Drawings

CIS-4A-ARYL, 1, 2, 3, 4, 4A, 9B-HEXAHYDRO-BENZOFURO-[3,2-C]-PYRIDINES USEFUL AS ANALGESICS

This is a division, of application Ser. No. 400,576 filed July 22, 1982, now U.S. Pat. No. 4,507,306.

This invention relates to novel cis-4a-aryl-1,2,3,4,4a,9b-hexahydro-benzofuro[3,2-c]pyridines of the formula

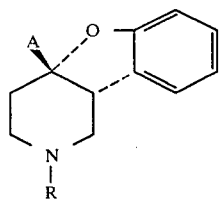
(I)

wherein A is

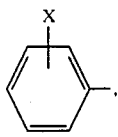

2-furyl or 3-furyl, X being hydrogen, halogen, methyl, methoxy or hydroxyl; and R is, independently of A, hydrogen, loweralkyl, cyanoloweralkyl, loweralkenyl, phenylloweralkyl, phenylcarbonylloweralkyl, phenoxyloweralkyl or cycloalkylloweralkyl, which have primary utilities as analgesic and anticonvulsant agents; to pharmaceutical compositions comprising said compounds as active ingredients; to methods of treatment with pharmaceutically effective amounts of said compounds; and to method of synthesizing said compounds.

This invention also relates to novel 3-o-fluorophenyl-1-methyl-4-aryl-4-piperidinols of the formula

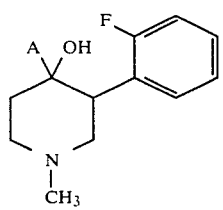
(II)

where A is as defined above except that A may not be hydroxyphenyl, which are useful as intermediates for synthesizing aforementioned compounds, and to methods of synthesizing same. Some of these compounds are also useful as analgesic agents and/or anticonvulsant agents.

Unless otherwise stated or indicated, the term "alkyl" as used throughout the specification and the appended claims denotes a straight or branched saturated hydrocarbon radical.

Unless otherwise stated or indicated, the term "loweralkyl" denotes an alkyl group having from 1 to 6 carbon atoms.

The term "loweralkenyl" denotes a straight or branched unsaturated hydrocarbon radical having from 2 to 6 carbon atoms and a double bond.

The term "phenylloweralkyl" denotes a loweralkyl group having attached thereto a phenyl or a mono-halogen-substituted phenyl group.

The term "phenylcarbonylloweralkyl" denotes a loweralkyl group having attached thereto a benzoyl or a mono-halogen ring substituted benzoyl group, including situations where the carbonyl group is in the ethylene ketal form.

The term "phenoxyloweralkyl" denotes a loweralkyl group having attached thereto a phenoxy or mono-halogen substituted phenoxy group.

The term cycloalkylloweralkyl" denotes a loweralkyl group having attached thereto a saturated hydrocarbon ring of from 3 to 7 ring carbons.

Unless otherwise stated, the term "halogen" as used herein includes fluorine, chlorine, bromine and iodine.

In the formulas presented herein substituents attached to the hexahydropyridine (piperidine) ring system may be in either the cis or trans configuration, i.e., the substituents may be respectively on the same side or on opposite sides of the average plane of the piperidine ring. Unless otherwise specified, each formulas covers both the cis and trans isomers. In the structural formula used herein, heavy lines (–) indicate the substituent is above the average plane of the piperidine ring and broken lines (- -) indicate the substituent is below the average plane of the ring. A light line (-) indicates the substituent may be above or below the average plane of the ring.

One of the starting compounds of this invention 3-o-fluorophenyl-1-methyl-4-piperidone of formula III may be prepared, for instance, from o-fluorobenzyl chloride by the following Reaction Scheme A.

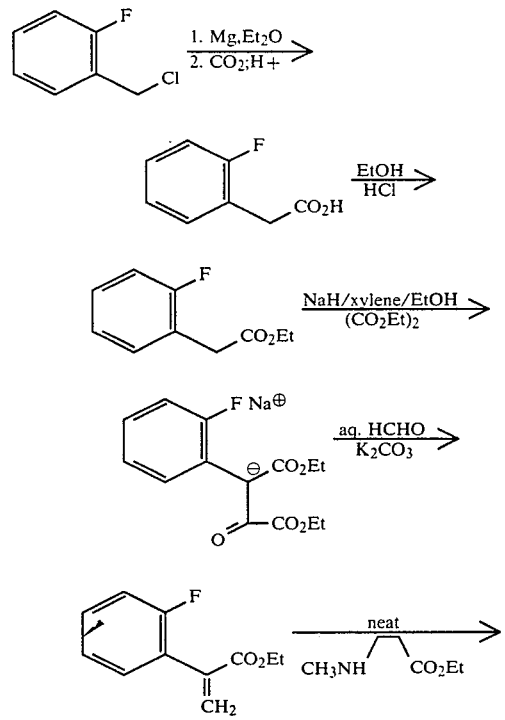

-continued
REACTION SCHEME A

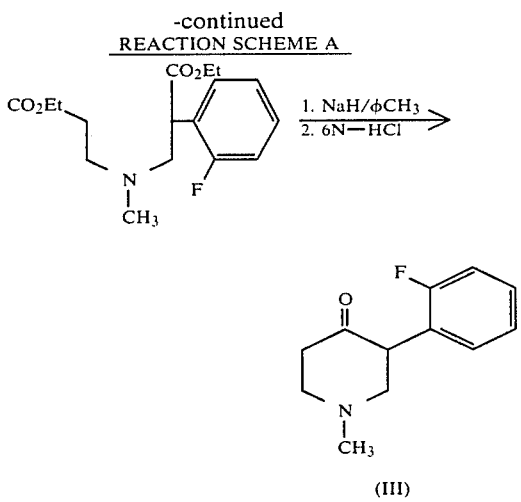

(III)

After the compound III has been synthesized, 3o-fluorophenyl-1-methyl-4-phenyl-4-piperidinols of formula V may be prepared by reacting the compound III with an organometallic reagent of formula IV where M is Li or MgHal wherein Hal is chloride, bromide, or iodide, and $X_1$ is hydrogen, halogen, methyl or methoxy, and treating the resultant product with a suitable protic compound such as water.

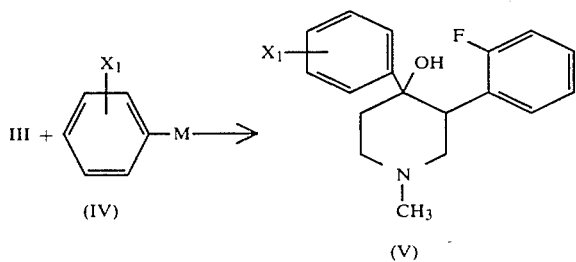

It is more convenient to use the lithio derivative

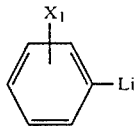

than to use the Grignard reagent for this reaction. Said lithium compound is prepared, for instance, by treating bromobenzenes of the formula

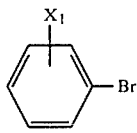

dissolved or suspended in an ethereal solvent such as diethylether, dimethoxyethane, dioxane, tetrahydrofuran or the like, with a lower alkyllithium such as methyllithium, ethyllithium, n-butyllithium or the like in an inert hydrocarbon solvent such as pentane, hexane, heptane or the like. n-Butyllithium in hexane is preferred as is tetrahydrofuran as the ethereal solvent.

The aforementioned condensation between compound III and compound IV where M is lithium is conveniently carried out without isolation of the preformed lithio derivative at an initial reaction temperature of about −70° to −20° C., a range of about −60° to −40° C. being preferred, and a final reaction temperature of about −70° to 20° C.

By varying the identity and the substitution site of $X_1$ in the aforementioned bromobenzenes, one can control the identity and the position of $X_1$ in the compounds V.

It is, of course, understood that compounds V include the stereoisomers thereof and such isomers fall within the scope of the invention disclosed herein. Namely, compounds V include both cis and trans isomers. The relative proportions of the two depend on the identity of the substituent $X_1$ and the reaction condition, but usually the cis 4-hydroxy-3-(2-fluorophenyl) isomer is favored over the trans isomer. Typical values of the proportions are 85–95% for the cis isomer and 5–15% for the trans isomer.

After the aforementioned condensation reaction between compounds III and IV, the reaction mixture is poured into water and the piperidinol product is usually extracted from the mixture with ether. The ether extract is dried and thereafter evaporated in vacuo to afford crude crystals. They are recrystallized from a suitable medium such as isopropanol. It has been observed that this procedure alone often affords substantially pure cis isomers. Where it is desired to isolate the trans isomer, it can be accomplished, for instance, by subjecting a mixture of cis and trans isomers to column chromatography on silica gel with acetone as an eluant. Usually the trans isomer is less polar than the cis isomer. This procedure usually affords substantially pure trans isomer.

The compounds V are converted to compounds of formula VI by a ring closure which may be effected by use of a strong base, such as for instance, sodium hydride, phenyllithium, etc.

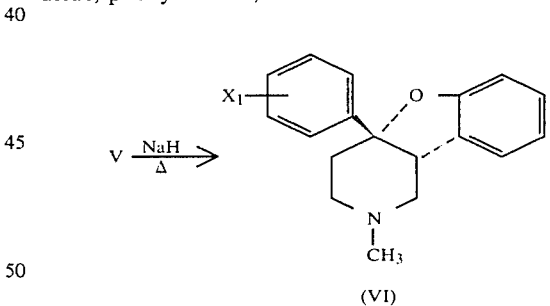

(VI)

The cis isomers of the piperidinol compounds V, when allowed to react with sodium hydride, give the corresponding cis isomers of compounds VI. However, it has been observed that the trans isomers of compounds V give a mixture of the cis isomers of compounds VI and the cis isomers of piperidinols V, with very little yield of the trans isomers of compounds VI. For this reason, the cis isomers of the piperidinol compounds V are preferred over the trans isomers.

After the compounds VI have been obtained, various substituents R as defined earlier can be introduced to the nitrogen atom. For this purpose, the methyl group of compounds VI is first converted to hydrogen to obtain compounds VII. Thereafter the secondary amine hydrogen of compounds VII is replaced with various groups.

Thus, compound VI is allowed to react with ethyl chloroformate and the resultant carbamate hydrolyzed to afford secondary amine compounds VII. The carbamation may be conducted, for instance, in benzene under reflux in the presence of potassium carbonate. The hydrolysis of the carbamate may be conducted, for instance, in ethanol-water under reflux in the presence of sodium hydroxide.

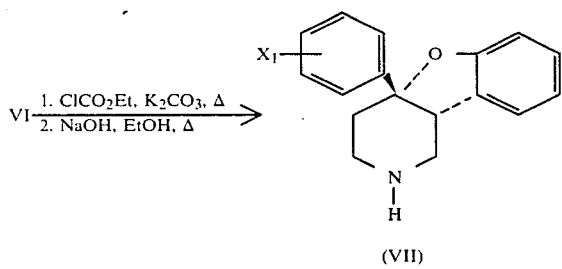

A variety of derivatives can be obtained from compounds VII by replacing the amine hydrogen with various other groups. In the next several paragraphs, the term "derivative of compound VII" means a compound derived by such a replacement at the nitrogen atom of compound VII.

Thus, reaction of compound VII with cyclopropane carbonyl chloride affords the cyclopropylcarbonyl derivative of compound VII. Said reaction may be conducted, for instance, in the presence of triethylamine in a suitable solvent such as chloroform at room temperature. Reduction of the carbonyl group of said cyclopropylcarbonyl derivative by use of, for instance, LiAlH$_4$ affords cyclopropylmethyl derivative of compound VII. The reduction may be conducted in THF under reflux.

Similarly, reaction of compound VII with phenylacetyl chloride under conditions analogous to those above affords the phenylacetyl derivative of compound VII. Reduction of the carbonyl group of the phenylacetyl derivative under analogous conditions affords the phenethyl derivative of compound VII.

Compounds VII react wth various alkyl halides to afford N-alkyl derivatives thereof. Alkyl bromides and chlorides are preferred reagents for the purpose of the alkylation.

Thus, reaction of compound VII with 1-bromo-3-methyl-2-butene affords the 3-methyl-2-butenyl derivative of compound VII. The reaction may be conducted, for instance, in dry dimethylformamide in the presence of potassium carbonate at a temperature of from 60° to 85° C.

Under analogous reaction conditions, reaction of compound VII with 3-phenoxypropyl bromide affords the 3-phenoxypropyl derivative of compound VII. Reaction of compound VII with allyl bromide affords the allyl derivative thereof. Reaction of compound VII with 1-bromo-3-phenylpropane affords the 3-phenylpropyl derivative thereof. Reaction of compound VII with γ-chloro-4-fluorobutyrophenone ethylene ketal affords a derivative having the ethylene ketal form of 3-(4-fluorobenzoyl)propyl attached to the nitrogen. Hydrolysis of this derivative, for instance, in hydrochloric acid-methanol medium at room temperature affords the 3-(4-fluorobenzoyl)propyl derivative of compound VII. Reaction of compound VII with acrylonitrile affords the 2-cyanoethyl derivative thereof. Reaction of compound VII with chloroacetonitrile affords the cyanomethyl derivative thereof.

The various reactions of compound VII described above which introduce various substituents on the nitrogen atom are schematically shown in Reaction Scheme B. The wavy lines are used in the scheme in order to avoid repetitive drawing of the same moiety.

REACTION SCHEME B

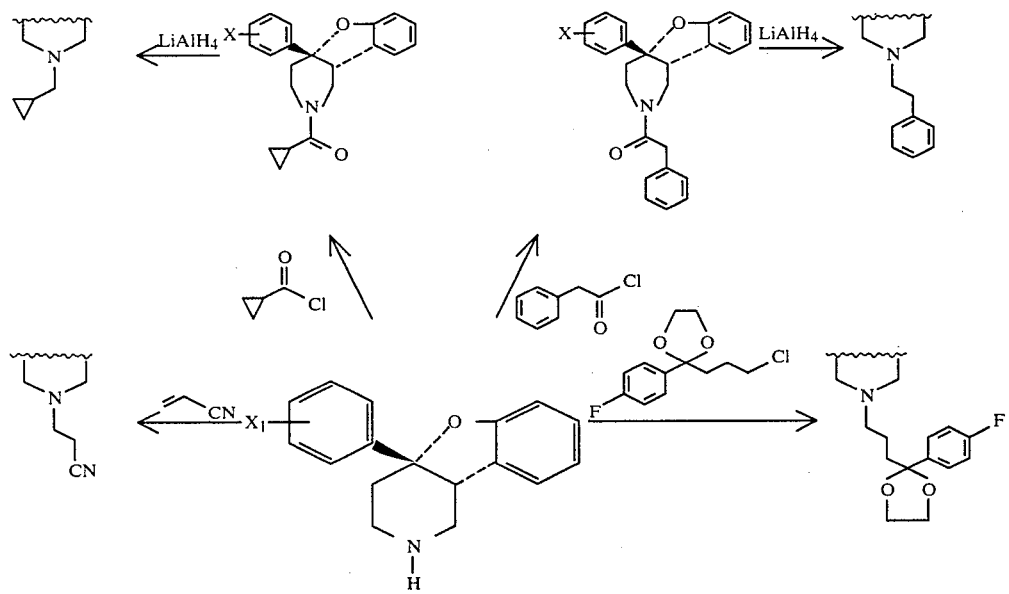

-continued
REACTION SCHEME B

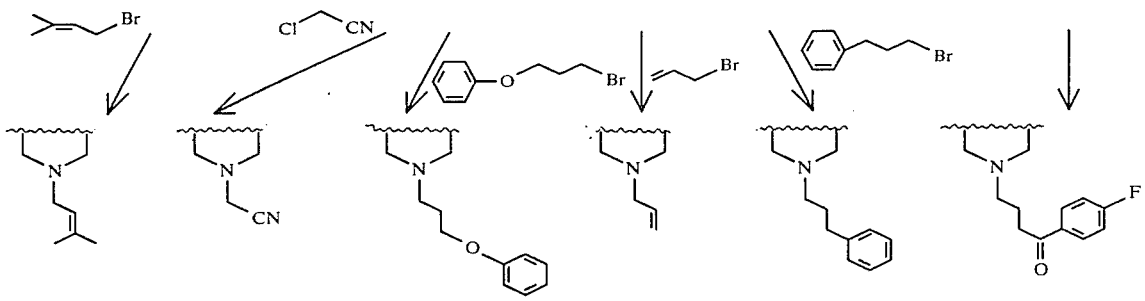

A methoxy group attached to the benzene ring in compounds of the formula,

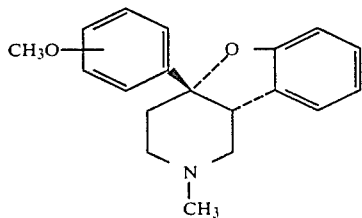

(VIII)

where R is as defined in formula I, may be converted to a hydroxyl group. A preferred method for achieving this conversion is to dissolve the methoxy compound and lithium thiomethoxide in a suitable solvent such as dry hexamethylphosphoramide and heat the mixture under a drying tube at a temperature of from 120° to 160° C. After the reaction mixture is allowed to cool, water is added thereto and the pH adjusted to neutral by adding an acid such as hydrochloric acid.

By virtue of the conversion reaction of compound VI to compound VII, the various reactions for compound VII described in Reaction Scheme B, and said conversion of the methoxy group of compound VIII to a hydroxy group, one obtains compounds of the general formula,

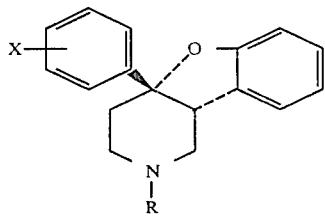

(IX)

where X and R are as defined in formula I. It should be noted that the substituent $X_1$ in formula VI and VII is not the same as the substituent X in Formula I and IX; the former does not include the hydroxy group, whereas the latter does.

When the compound III is allowed to react with 2-furyllithium, 3-o-fluorophenyl-4-(2-furyl)-1-methyl-4-piperidinol is obtained. The 2-furyllithium may be prepared, for instance, by reacting furan in THF with n-butyllithium in hexane at a low temperature of, for instance, from −30° to 0° C. Without isolating the 2-furyllithium from the mixture, compound III in a suitable solvent such as THF is added to the mixture and the reaction is conducted at room temperature. The resultant cis piperidinol compound is allowed to undergo ring closure reaction to afford compound X under conditions analogous to those described earlier for the ring closure of compounds V. This series of reactions is shown in Reaction Scheme C. It should be noted that if one starts out with 3-furyllithium, the corresponding 3-furyl derivates of the above-mentioned piperidinol and of compound X are obtained.

REACTION SCHEME C

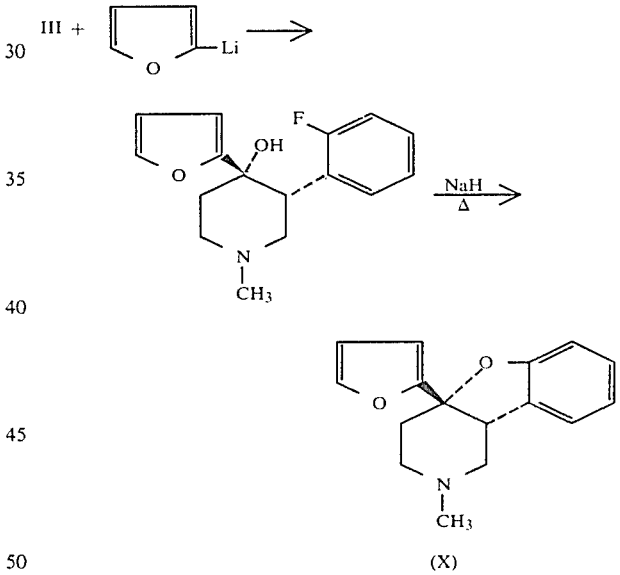

It sould be noted that the methyl group in compound X can be replaced by various substituents in much the same manner described earlier for converting the N-methyl compound VI into other derivatives.

Compounds of the present invention are useful as analgesics due to their ability to alleviate pain in mammals, as demonstrated in the p-phenylbenzoquinone writhing assay in mice, a standard assay for analgesia [Proc. Soc. Exptl. Biol. Med., 95, 729 (1957)]. Thus, for instance, cis-1,2,3,4,4a,9b-hexahydro-2-methyl-4a-phenyl-benzofuro[3,2-c]pyridine hydrochloride, cis-1,2,3,4,4a,9b-hexahydro-4a-phenyl-benzofuro[3,2-c]pyridine, cis-2-cyclopropylmethyl-1,2,3,4,4a,9b-hexahydro-4a-phenyl-benzofuro [3,2-c]pyridine hydrochloride, cis-1,2,3,4,4a,9b-hexahydro-2-phenethyl-4a-phenyl-benzofuro[3,2-c]pyridine hydrochloride, cis-4a-(4fluorophenyl)-1,2,3,4,4a,9b-hexahydro-2-methyl-benzofuro[3,2-c]pyridine hydrochloride, cis-4a-(3-fluorophenyl)-1,2,3,4,4a,9b-hexahydro-benzofuro[3,2-c]pyridine maleate, and cis-3-o-fluorophenyl-1-methyl-4-o-tolyl-4-piperidinol, respectively, have $ED_{50}$ values of 9.4, 8.4, 9.6, 15.2, 6.4, 2.8 and 2.5 mg subcutaneous dose per kg of body weight for the inhibition of writhing produced in this assay. At a subcutaneous dose of 10 mg/kg of body weight cis-4a-(4-chlorophenyl)-1,2,3,4,4a,9b-hexahydro-2-methyl-benzofuoro[3,2-c]pyridine hydrochloride and cis-3-o-fluorophenyl-4-(2-furyl)-1-methyl-4-piperidinol demonstrate, respectively, a 65% and 68% inhibition of writhing in this assay. These data illustrate that compounds of this invention are useful for alleviating pain in mammals when administered in amounts ranging from about 0.1 to about 100 mg/kg of body weight per day.

Compounds of the present invention are also useful as anticonvulsant agents for mammals, as determined by the method of Woodbury, L. A. and Davenport, V. D. (Arch., Inc. Pharmacodynam, 92, pp. 97–107 (1952). For example, cis-1,2,3,4,4a,9b-hexahydro-2-methyl-4a-phenyl-benzofuro[3,2-c]-pyridine hydrochloride had an $ED_{50}$ value of 64 mg intraperitoneal dose per kg of body weight for the protection from the supramaximal electroshock; at 25 mg per kg body weight intraperitoneal dose, cis-1,2,3,4,4a,9b-hexahydro-4a-phenyl-benzofuro[3,2-c]pyridine, cis-2-[3-(4-fluorobenzoyl)-propyl]-1,2,3,4,4a,9b-hexahydro-4a-phenyl-benzofuro[3,2-c]pyridine maleate, and cis-2-allyl-1,2,3,4,4a,9b-hexahydro-4a-phenyl-benzofuro[3,2-c]pyridine maleate respectively produced 33%, 50% and 50% protection from the supramaximal electroshock; at a 20 mg/kg intraperitoneal dose, cis-3-o-fluorophenyl-1-methyl-4-o-tolyl-4-piperidinol demonstrated a 100% protection from the supramaximal electroshock; and cis-3-o-fluorophenyl-4-m-fluorophenyl-1-methyl-4-piperidinol and cis-4-m-chlorophenyl-3-o-fluorophenyl-1-methyl-4-piperidinol respectively had $ED_{50}$ values of 8.8 and 15.2 mg/kg intraperitoneal dose for the protection from the supramaximal electroshock.

Anticonvulsant activities of the compounds of the present invention are also demonstrated by the metrazol lethality test in mice. In this test, groups of male, CD-1 mice, (18–30 grams each) are utilized. Test drugs are prepared using distilled water and, if insoluble, a suitable surfactant is added. The route of administration may be varied (p.o., i.p., s.c.) but all administrations are in volumes proportional to 10 cc/kg.

For a time response, 5 groups (6/group) are administered drug orally at 30, 60, and 120 minutes prior to metrazol treatment. Control animals (2/group) receive vehicle. Metrazol (pentamethylene-tetrazol) is prepared at a concentration of 150 mg/10 ml in distilled water. Metrazol is administered intraperitoneally to all animals at 150 mg/kg in distilled water. Those animals alive 15 minutes after metrazol injection are considered protected. The time period with the greatest percent protected is called peak time of drug activity.

A dose range is run in the same manner as a time response except that 50 animals (10/group) are tested at the peak time of drug activity. One group receives vehicle. An $ED_{50}$ is calculated by means of linear regression analysis. Diazepam, which is a standard anticonvulsant agent, has an $ED_{50}$ value of 1.43 mg/kg p.o. in this test.

At an oral dose of 50 mg per kg of body weight, cis-1,2,3,4,4a,9b-hexahydro-2-methyl-4a-phenyl-benzofuro[3,2-c]pyridine hydrochloride, cis-1,2,3,4,4a,9b-hexahydro-4a-phenyl-benzofuro[3,2-c]pyridine, and cis-2-allyl-1,2,3,4,4a,9b-hexahydro-4a-phenyl-benzofuro[3,2-c]pyridine maleate respectively produced 17%, 67% and 17% protection in said metrazol test. Cis-3-o-fluorophenyl-1-methyl-4-o-tolyl-4-piperidinol and cis-3-o-fluorophenyl-4-m-fluorophenyl-1-methyl-piperidinol had $ED_{50}$ values of 7.5 and 20.7 mg/kg, p.o., respectively; and at an oral dose of 40 mg/kg body weight, cis-3-o-fluorophenyl-1-methyl-4-phenyl-4-piperidinol produced 80% protection.

These data illustrate that compounds of the present invention are useful in treating convulsions in mammals when administered in amounts ranging from about 1.0 to about 150 mg/kg of body weight per day.

Effective quantities of the compounds of the invention may be administered to a patient by any one of various methods, for example, orally as in capsules or tablets, parenterally in the form of sterile solutions or suspensions, and in some cases intraveneously in the form of sterile solutions. The free base final products, while effective themselves, may be formulated and administered in the form of their pharmaceutically acceptable addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixiers, suspensions, syrups, wafers, chewing gum and the like. The preparations should contain at least 0.5% of active compound, but may be varied depending upon the particular form and may conveniently be between 47% to about 70% of the weight of the unit. The amount of active compound in such compositions is such that a suitable dosage will be obtained. Preferred compositions and preparations according to the present invention are prepared so that an oral dosage unit form contains 1.0 to 300 milligrams of active compound.

The tablets, pills, capsules, troches and the like may also contain the followng ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as collodial silicon dioxide; and a sweetening agent such as sucrose or saccharin; and a flavoring agent such as peppermint, methyl salicylate, or orange flavoring. When the dosage unit is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapuetic administration, the active compounds of the invention may be incorporated into a solution or suspension. These preparations should contain a pharmaceutically effective amount, i.e. at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The invention is illustrated by the following examples wherein unless indicated otherwise, the temperature indicated is in degrees Centigrade.

EXAMPLE 1

(a)

cis-3-o-Fluorophenyl-1-methyl-4-phenyl-4-piperidinol

To 40 ml of anhydrous ether under nitrogen was added 21.74 ml of 2.3 M phenyllithium in 70:30 benzene/ether. To this solution was added dropwise with stirring at such a rate as to maintain a gentle reflux a solution of 3.11 g of 3-o-fluorophenyl-1-methyl-4-piperidone in 35 ml of anhydrous ether. The resulting mixture was stirred at ambient temperature for 3 hours. The reaction mixture was then poured into 100 ml of water and extracted with ether (2×100 ml). The combined extracts were dried over anhydrous $Na_2SO_4$ and evaporated in vacuo to give 4.91 g of solid. Recrystallization from isopropanol afforded 2.43 g (56.8%) of colorless crystals, m.p. s 150, 154°–157°.

ANALYSIS: Calculated for $C_{18}H_{20}FNO$: 75.76%C; 7.07%H; 4.91%N; 6.66%F; Found: 76.16%C; 7.13%H; 4.88%N; 6.56%F.

(b)

trans-3-o-Fluorophenyl-1-methyl-4-phenyl-4-piperidinol

To 400 ml of anhydrous ether under nitrogen was added from a dropping funnel 190.5 ml of 2.1 M phenyllithium in 70:30 benzene/ether. To this solution was added dropwise with stirring at such a rate as to maintain a gentle reflux a solution of 24.87 g of 3-o-fluorophenyl-1-methyl-4-piperidone in 200 ml of anhydrous ether. The resulting mixture was stirred at ambient temperature for 4 hours. The reaction mixture was poured into 800 ml of water and extracted with ether (2×800 ml). The combined extracts were dried over anhydrous $Na_2SO_4$ and evaporated in vacuo to give 43.94 g of solid. Recrystallization from isopropanol afforded 13.58 g of pure cis isomer as colorless crystals, m.p. s 151, 156°–159°.

The mother liquors from the recrystallization were concentrated in vacuo to approximately 75 ml and allowed to stand overnight before cooling. The crystalline material was filtered, washed with cold isopropanol and petroleum ether, and dried to give 4.27 g of colorless crystals, m.p. s 130, 133°–145°. This material was shown by NMR to an approximately 2:1 mixture of trans/cis alcohols: total yield 17.85 g (52.1%).

The mixture of alcohols from above was chromatographed on 125 g of silica gel with acetone as eluant until the less polar trans alcohol was eluted and then with 25% MeOH/acetone as eluant until all of the cis product had been eluted.

The fractions containing the trans alcohol were combined and evaporated in vacuo to afford 2.60 g (7.6%) of pure trans isomer as colorless crystalline solid, m.p. 159°–161°. A 0.25 g portion of this material was recrystallized from isopropanol to provide 0.18 g of crystals, m.p. s 159, 160°–161°.

ANALYSIS: Calculated for $C_{18}H_{20}FNO$: 75.76%C; 7.07%H; 4.91%N; 6.66%F; Found: 75.90%C; 7.31%H; 4.65%N; 6.92%F.

EXAMPLE 2 cis-1,2,3,4,4a,9b-Hexahydro-2-methyl-4a-phenyl-benzofuro[3,2-c]pyridine hydrochloride A suspension of 7.79 g of 3-o-fluorophenyl-1-methyl-4-phenyl-4-piperidinol (>90% cis) and 1.05 g of sodium hydride in 55 ml of dry benzene was heated to reflux under nitrogen and 55 ml of dry dimethylformamide was added. The resulting mixture was heated at reflux for 2½ hours. As TLC analysis indicated a small amount of alcohol to be present, an additional 0.12 g of NaH was added and the mixture refluxed an additional ½ hour. TLC analysis at this point indicated that the small amount of trans product formed at 2½ hours reflux seemed to be disappearing, presumably isomerizing to the cis product. The cooled reaction mixture was cautiously poured into 350 ml of water and extracted with ether (2×250 ml). The combined extracts were washed with water (3×250 ml), dried over anhydrous $Na_2SO_4$ and evaporated in vacuo to afford 7.35 g of an oil.

This material was dissolved in 100 ml of ether and treated with 50 ml of ether saturated with hydrogen chloride. The solvent was removed in vacuo. The residue was triturated with ether, filtered, and dried to give 7.69 g (93.3%) of crystalline solid. Recrystallization from ethanol afforded 6.31 g (76.6%) of colorless crystals, m.p. s 270, 273.5°–275.5°.

ANALYSIS: Calculated for $C_{18}H_{19}NO.HCl$: 71.63%C; 6.68%H; 4.64%N; 11.75%Cl; Found: 71.45%C; 6.60%H; 4.65%N; 11.54%Cl.

EXAMPLE 3 cis-2-Ethoxycarbonyl-1,2,3,4,4a,9b-hexahydro-4a-phenyl-benzofuro[3,2-c]-pyridine To a stirred solution of 4.25 g of cis-1,2,3,4,4a,9b-hexahydro-2-methyl-4a-phenyl-benzofuro[3,2-c]pyridine in 35 ml of dry benzene was added 3.32 g of anhydrous potassium carbonate and 2.60 g of ethyl chloroformate. The resulting mixture was heated at reflux under nitrogen for 32 hours. The cooled reaction mixture was poured into 100 ml of water and extracted with ether (2×100 ml). The combined ether extracts were washed with 2N HCl (2×20 ml). During the first washing some solid separated out. This material was filtered off, combined with the acid washings, and set aside. The ether extracts were washed with 50 ml of brine, dried over anhydrous Na$_2$SO$_4$, and evaporated in vacuo to afford 3.59 g of an oil.

The aqueous acidic layer (containing the filtered solid) was cooled to 0°, basified with 50% aq. NaOH, and extracted with methylene chloride (2×40 ml). After drying over anhydrous Na$_2$SO$_4$ and evaporation of the solvent in vacuo 0.74 g of the starting compound was recovered. This material was resubmitted to the reaction conditions for 24 hours, worked up and partitioned as described above. In this manner an additional 0.59 g of carbamate was obtained as an oil. The total yield of the ethyl carbamate was 4.18 g (80.8%)

ANALYSIS: Calculated for C$_{20}$H$_{21}$NO$_3$: 74.28%C; 6.55%H; 4.33%N; Found: 73.92%C; 6.66%H; 3.96%N.

EXAMPLE 4 cis-1,2,3,4,4a,9b-Hexahydro-4a-phenyl-benzofuro[3,2-c]pyridine

To a solution of 3.56 g of cis-2-ethoxycarbonyl-1,2,3,4,4a,9b-hexahydro-benzofuro[3,2-c]pyridine in 42 ml of absolute ethanol was added 28 ml of 20% aqueous NaOH solution. The resulting mixture was heated at reflux under nitrogen for 32 hours. Most of the ethanol was removed in vacuo. The residue was diluted with 50 ml of water and extracted with methylene chloride (2×100 ml). There were initially some problems with emulsions. The combined extracts were dried over anhydrous Na$_2$SO$_4$ and evaporated in vacuo to give 2.72 g (98.4%) of crystalline solid. Recrystallization from hexane afforded 1.98 g (71.6%) of crystals, m.p. s 91, 95°–98°.

ANALYSIS: Calculated for C$_{17}$H$_{17}$NO: 81.24%C; 6.82%H; 5.57%N; Found: 81.09%C; 6.88%H; 5.38%N.

EXAMPLE 5 cis-2-Cyclopropylcarbonyl-1,2,3,4,4a,9b-hexahydro-4a-phenyl-benzofuro-[3,2-c]pyridine To a solution of 3.77 g of cis-1,2,3,4,4a,9b-hexahydro-4a-phenylbenzofuro[3,2-c]pyridine in 100 ml of chloroform containing 1.67 g of triethylamine was added dropwise with stirring under nitrogen a solution of 1.65 g of cyclopropane carbonyl chloride in 25 ml of chloroform. The reaction mixture was stirred at room temperature for 4 hours, diluted with 100 ml of chloroform and washed with 100 ml of 2N HCl and 100 ml of 10% aqueous NaOH. The organic layer was dried over anhydrous Na$_2$SO$_4$ and evaporated in vacuo to afford 4.70 g (98.1%) of a glass.

ANALYSIS: Calculated for C$_{21}$H$_{21}$NO$_2$: 78.97%C; 6.63%H; 4.39%N; Found: 78.77%C; 6.70%H; 4.11%N.

EXAMPLE 6 cis-2-Cyclopropylmethyl-1,2,3,4,4a,9b-hexahydro-4a-phenyl-benzofuro-[3,2-c]pyridine hydrochloride To a suspension of 1.03 g of lithium aluminum hydride in 100 ml of dry tetrahydrofuran was added dropwise with stirring under nitrogen a solution of 4.31 g of cis-2-cyclopropylcarbonyl-1,2,3,4,4a,9b-hexahydro-4a-phenyl-benzofuro[3,2-c]pyridine in 35 ml of dry tetrahydrofuran. The resulting mixture was heated at reflux under nitrogen for 3 hours. Excess LiAlH$_4$ was decomposed by cautious dropwise addition of saturated aqueous Na$_2$SO$_4$ at 0° under nitrogen. The precipitate was filtered off and washed repeatedly with 1:1 ether/tetrahydrofuran. The combined filtrate and washings were dried over anhydrous Na$_2$SO$_4$ and evaporated in vacuo to afford 5.02 g of an oil. This material was dissolved in 50 ml of ether and treated with 25 ml of ether saturated with hydrogen chloride gas. The solvent was removed in vacuo and the residue triturated with ether, filtered, and dried to afford 4.29 g (93.0%) of crystalline solid. Recrystallization from ethanol gave 3.23 g (70.0%) of crystals, m.p. s 237, 256°–259°.

ANALYSIS: Calculated for C$_{21}$H$_{23}$NO.HCl: 73.77%C; 7.08%H; 4.10%N; 10.37%Cl; Found: 73.78%C; 7.17%H; 4.02%N; 10.30%Cl.

EXAMPLE 7 cis-1,2,3,4,4a,9b-Hexahydro-4a-phenyl-2-phenylacetyl-benzofuro[3,2-c]pyridine one third ethanolate To a solution of 3.02 g of cis-1,2,3,4,4a,9b-hexahydro-4a-phenylbenzofuro[3,2-c]pyridine in 80 ml of chloroform containing 1.34 g of triethylamine was added dropwise with stirring under nitrogen a solution of 1.86 g of phenylacetyl chloride in 20 ml of chloroform. The resulting solution was stirred for 3 hours, diluted with 80 ml of chloroform, and washed with 80 ml of 2N HCl and 80 ml of 10% aqueous NaOH. The organic layer was dried over anhydrous Na$_2$SO$_4$ and evaporated in vacuo to give 4.80 g of an oil. This material was chromatographed on 125 g of silica gel using 2% MeOH/CHCl$_3$ as an eluant. The enriched fractions were combined and evaporated in vacuo to afford 4.20 g (94.7%) of a glass. A 0.5 g portion of this material was taken up in a minimum amount of hot ethanol, cooled, filtered, and dried at 40° for one hour to give 0.42 g of crystals m.p. s 61, 70°–73°. These crystals were shown by NMR to contain 0.9 mole of ethanol. Additional drying at 40° (3 hours) gave crystalline solid, m.p. s 50, 54°–60°. NMR showed this material to contain one-third a molecule of ethanol per molecule of the product compound.

ANALYSIS: Calculated for C$_{25}$H$_{23}$NO$_2$.⅓C$_2$H$_5$OH: 80.11%C; 6.55%H; 3.64%N; Found: 80.04%C; 6.48%H; 3.40%N.

EXAMPLE 8 cis-1,2,3,4,4a,9b-Hexahydro-2-phenethyl-4a-phenyl-benzofuro[3,2-c]pyridine hydrochloride To a suspension of 0.76 g of lithium aluminum hydride in 70 ml of dry tetrahydrofuran was added dropwise with stirring under nitrogen a solution of 3.69 g of cis-1,2,3,4,4a,9b-hexahydro-4a-phenyl-2-phenylacetyl-benzofuro[3,2-c]pyridine in 30 ml of dry tetrahydrofuran. The resulting mixture was heated at reflux for 3 hours. Excess LiAlH$_4$ was decomposed by cautious dropwise addition of saturated aqueous Na$_2$SO$_4$ at 0° under nitrogen. The precipitate was filtered off and washed repeatedly with 1:1 ether/tetrahydrofuran. The combined filtrate and washings were dried over anhydrous Na$_2$SO$_4$ and evaporated in vacuo to afford 3.35 g (94.2%) of an oil.

This material was dissolved in 50 ml of ether and treated with 25 ml of ether saturated with HCl. The solvent was removed in vacuo, and the residue was triturated with ether, filtered, and dried to give 3.29 g (83.9%) of crystalline solid, m.p. s 237, 241°–245°. Recrystallization from ethanol afforded 2.80 g (71.4%) of colorless crystals, m.p. s 235, 244°–248° (with bubbling).

ANALYSIS: Calculated for C$_{25}$H$_{25}$NO.HCl: 76.61%C; 6.69%H; 3.57%N; Found: 76.38%C; 6.67%H; 3.27%N.

EXAMPLE 9 cis-1,2,3,4,4a,9b-Hexahydro-2-(3-methyl-2-butenyl)-4a-phenyl-benzofuro[3-2c]pyridine hydrochloride To a solution of 3.77 g of cis-1,2,3,4,4a,9b-hexahydro-4a-phenyl benzofuro[3,2-c]pyridine in 60 ml of dry dimethylformamide was added 4.5 g of anhydrous $K_2CO_3$ and 2.46 g of 1-bromo-3-methyl-2-butene. The resulting suspension was heated at 80° under nitrogen for 18 hours. The cooled reaction mixture was diluted with 500 ml of ether and washed with water (4×300 ml). The ether layer was dried over anhydrous $Na_2SO_4$ and evaporated in vacuo to give 4.13 g (86.2%) of an oil.

This material was dissolved in 75 ml of ether and treated with 25 ml of ether saturated with HCl. The solvent was removed in vacuo, and the residue triturated with ether, filtered, and dried to provide 3.67 g (68.7%) of crystalline solid, m.p. s 210, 222°–224.5° (with bubbling). Recrystallization from acetone afforded 2.89 g (54.1%) of crystalline solid, m.p. s 229, 230°–232° (with bubbling).

Analysis: Calculated for $C_{22}H_{25}NO.HCl$: 74.24%C; 7.36%H; 3.94%N; Found: 74.12%C; 7.28%H; 3.85%N.

EXAMPLE 10 cis-1,2,3,4,4a,9b-Hexahydro-4a-phenyl-2-(3-phenylpropyl)-benzofuro[3,2-c]-pyridine maleate To a solution of 3.02 g of cis-1,2,3,4,4a,9b-hexahydro-4a-phenylbenzofuro[3,2-c]pyridine in 48 ml of dry dimethylformamide was added 3.6 g of anhydrous potassium carbonate and 2.59 g of 1-bromo-3-phenylpropane. The resulting suspension was heated at 80° under nitrogen for 19 hours. The cooled reaction mixture was diluted with 500 ml of ether and washed with water (4×250 ml). The organic layer was dried over anhydrous $Na_2SO_4$ and evaporated in vacuo to provide 4.50 g of an oil.

This material was dissolved in 50 ml of ether and treated with a solution of 1.74 g of maleic acid dissolved in 15 ml of ether and 10 ml of absolute ethanol. After stirring for 15 minutes, the precipitated salt was filtered, washed with ether, and dried to give 4.70 g (80.7%) of crystalline solid, m.p. s 161, 163°–165°. Recrystallization from ethanol afforded 4.25 g (72.9%) of crystalline solid m.p. s 165, 166°–167°.

ANALYSIS: Calculated for $C_{26}H_{27}NO.C_4H_4O_4$: 74.21%C; 6.43%H; 2.88%N; Found: 74.46%C; 6.45%H; 2.66%N.

EXAMPLE 11 cis-1,2,3,4,4a,9b-Hexahydro-2-(3-phenoxypropyl)-4a-phenyl-benzofuro[3,2-c]-pyridine maleate To a solution of 2.51 g of cis-1,2,3,4,4a,9b-hexahydro-4a-phenylbenzofuro[3,2-c]pyridine in 40 ml of dry dimethylformamide was added 3.0 g of anhydrous potassium carbonate and 2.32 g of 3-phenoxypropyl bromide. The resulting suspension was heated at 80° under nitrogen for 19 hours. The cooled reaction mixture was diluted with 400 ml of ether and washed with water (4×200 ml). The ether extracts were dried over anhydrous $Na_2SO_4$ and evaporated in vacuo to afford 3.97 g of an oil.

This material was dissolved in 50 ml of ether and treated with a solution of 1.45 g of maleic acid in 15 ml of ether and 10 ml of absolute ethanol. After stirring for 20 minutes, the precipitated salt was filtered, washed with ether, and dried to give 3.98 g (79.4%) of crystalline solid, m.p. s 140, 143°–144°. Recrystallization from ethanol afforded 3.74 g (74.6%) of crystalline solid, m.p. s 144, 144.5°–146°.

ANALYSIS: Calculated for $C_{26}H_{27}NO_2.C_4H_4O_4$: 71.83%C; 6.23%H, 2.79%N; Found: 71.70%C; 6.27%H; 2.55%N.

EXAMPLE 12 cis-2-Cyanomethyl-1,2,3,4,4a,9b-hexahydro-4a-phenyl-benzofuro[3,2-c]pyridine

To a solution of 3.02 g of cis-1,2,3,4,4a,9b-hexahydro-4a-phenyl-benzofuro[3,2-c]pyridine in 48 ml of dry dimethylformamide was added 3.6 g of anhydrous potassium carbonate and 0.982 g of chloroacetonitrile. The resulting suspension was heated at 80° under nitrogen for 19 hours. The cooled reaction mixture was dried with 500 ml of ether and washed with water (4×250 ml). The organic layer was dried over anhydrous $Na_2SO_4$ and evaporated in vacuo to give 3.48 g (99.9%) of a gum, which crystallized on standing. A 0.35 g portion of this material was recrystallized from ethanol to afford 0.22 g of crystals, m.p. s 93, 94°–96°.

ANALYSIS: Calculated for $C_{19}H_{18}N_2O$: 78.59%C; 6.25%H; 9.65%N; Found: 78.31%C; 6.07%H; 9.60%N.

EXAMPLE 13 cis-2-[3-(4-Fluorobenzoyl)propyl]-1,2,3,4,4a,9b-hexahydro-4a-phenylbenzofuro[3,2-c]pyridine ethylene ketal maleate To a solution of 2.51 g of cis-1,2,3,4,4a,9b-hexahydro-4a-phenylbenzofuro[3,2-c]pyridine in 40 ml of dry dimethylformamide was added 3.0 g of anhydrous $K_2CO_3$, 0.3 g of powdered KI, and 2.64 g of γ-chloro-4-fluorobutyrophenone ethylene ketal. The resulting suspension was stirred for 18 hours at 80° and then 29 hours at 100° under nitrogen. The cooled reaction mixture was diluted with 400 ml of ether and washed with water (4×200 ml). The organic layer was dried over anhydrous $Na_2SO_4$ and evaporated in vacuo to provide 4.97 g of a gum. A 0.368 g portion of this material was dissolved in 15 ml of ether and then treated with a solution of 0.116 g of maleic acid dissolved in 5 ml of ether and 2 ml of absolute ethanol. After stirring for 15 minutes, the mixture was cooled and the precipitated salt was filtered, washed with ether, and dried to give 0.29 g (63%) of crystalline solid, m.p. s 172, 177°–180°. Recrystallization from ethanol afforded 0.23 g (49.9%) of crystals, m.p. s 181 185°–187°.

ANALYSIS: Calculated for $C_{29}H_{30}FNO_3.C_4H_4O_4$: 68.85%C; 5.95% H; 2.43%N; Found: 68.52%C; 6.01%H; 2.24%N.

EXAMPLE 14 cis-2-[3-(4-Fluorobenzoyl)propyl]-1,2,3,4,4a,9b-hexahydro-4a-phenylbenzofuro[3,2-c]pyridine maleate To a solution of 2.51 g of cis-1,2,3,4,4a,9b-hexahydro-4a-phenylbenzofuro[3,2-c]pyridine in 40 ml of dry dimethylformamide was added 3.0 g of anhydrous $K_2CO_3$, 0.3 g of powdered KI, and 2.64 g of γ-chloro-4-fluorobutyrophenone ethylene ketal. The resulting suspension was heated for 18 hours at 80° and 29 hours at 100° under nitrogen. The cooled reaction mixture was diluted with 400 ml of ether and washed with water (4×200 ml). The ether layer was dried over anhydrous $Na_2SO_4$ and evaporated in vacuo to afford 4.97 g of a gum. A small amount of this material was purified as a maleate salt.

The remaining 4.60 g of material was dissolved in 30 ml of methanol and 20 ml of 3N HCl. A little oil separated out. The resulting mixture was stirred overnight (19 hours) at ambient temperature under $N_2$. Most of the methanol was removed in vacuo. The residue was diluted with 100 ml of water, cooled to 0°, and basified with 50% aqueous NaOH. Extraction with ether (2×125 ml), drying of the combined extracts with anhydrous $Na_2SO_4$, and evaporation in vacuo gave 4.12 g of an oil.

This material was dissolved in 50 ml of ether and treated with a solution of 1.16 g of maleic acid in 5 ml of absolute ethanol and 20 ml of ether. After some trituration and 15 minutes of stirring, the precipitated salt was filtered, washed with ether and dried to give 3.25 g (66.5%) of crystalline solid, m.p. s 128, 137°–143°. Recrystallization from ethanol afforded 2.59 g (53%) of crystalline solid, m.p. s 162, 165°–167°.

ANALYSIS: Calculated for $C_{27}H_{26}FNO_2.C_4H_4O_4$: 70.04%C; 5.69%H; 2.64%N; Found: 69.91%C; 5.62%H; 2.58%N.

EXAMPLE 15 cis-2-Allyl-1,2,3,4,4a,9b-hexahydro-4a-phenyl-benzofuro[3,2-c]pyridine maleate

To a solution of 3.02 g of cis-1,2,3,4,4a,9b-hexahydro-4a-phenylbenzofuro[3,2-c]pyridine in 48 ml of dry dimethylformamide was added 3.6 g of anhydrous $K_2CO_3$ and 1.60 g of allyl bromide. The resulting suspension was heated at 65° under nitrogen for 17 hours. The cooled reaction mixture was diluted with 500 ml of ether and washed with water (4×250 ml). The ether extracts were dried over anhydrous $Na_2SO_4$ and evaporated in vacuo to give 2.55 g (72.9%) of an oil.

This material was dissolved in 50 ml of ether and treated dropwise with stirring with a solution of 1.16 g of maleic acid dissolved in 5 ml of absolute ethanol and 20 ml of ether. After stirring for 30 minutes, the precipitated salt was filtered, washed with ether, and dried to provide 3.11 g (63.6%) of crystalline solid, m.p. s 155, 156°–157.5°. Recrystallization from ethanol gave 2.84 g (58.1%) of crystals, m.p. s 156, 158°–160°.

ANALYSIS: Calculated for $C_{20}H_{21}NO.C_4H_4O_4$: 70.74%C; 6.18%H; 3.44%N; Found: 70.47%C; 6.25%H; 3.42%N.

EXAMPLE 16 cis-2-(2-Cyanoethyl)-1,2,3,4,4a,9b-hexahydro-4a-phenyl-benzofuro[3,2-c]pyridine hydrochloride A 10 ml round bottom flask was charged with 0.503 g of cis 1,2,3,4,4a,9b-hexahydro-4a-phenyl-benzofuro[3,2-c]pyridine followed by 1 ml of acrylonitrile. The resulting mixture was stirred for ½ hour at room temperature under nitrogen and then heated at 60° for 1 hour. The reaction mixtue was diluted with 10 ml of ether and treated with 4 ml of ether saturated with HCl. After stirring for 15 minutes, the precipitated salt was filtered, washed with ether, and dried to give 0.68 g (99.8%) of crystalline solid, m.p. s 205, 213°–215°. Recrystallization from ethanol afforded 0.50 g (73.3%) of crystals, m.p. s 213, 216°–219°.

ANALYSIS: Calculated for $C_{20}H_{20}N_2O.HCl$: 70.47%C; 6.21%H; 8.22%N; Found: 70.43%C; 5.99%H; 8.31N.

EXAMPLE 17

(a)

cis-3-o-Fluorophenyl-4-p-methoxyphenyl-1-methyl-4-piperidinol

To a solution of 2.81 g of p-bromoanisole in 25 ml of anhydrous ether a −20° under nitrogen was added 6.82 ml of 2.2 M n-butyllithium in hexane. The resulting solution was stirred for 10 minutes at −20° and then warmed to room temperature. To this solution was added dropwise with stirring under nitrogen a solution of 1.24 g of 3-o-fluorophenyl-1-methyl-4-piperidone in 15 ml of dry ether. The resulting solution was stirred for 3 hours at room temperature, diluted with 50 ml of water, and extracted with ether (2×50 ml). The combined extracts were dried over anhydrous $Na_2SO_4$ and evaporated in vacuo to give 2.39 g of an oil, which smelled of anisole.

This material was chromatographed on 80 g of silica gel using acetone as eluant until the less polar trans isomer came off and then eluting with 25% MeOH/acetone. The fractions containing the more polar cis isomer (major product) were combined and evaporated in vacuo to afford 1.29 g (68.2%) of crystalline solid. Recrystallization from cyclohexane afforded 0.84 g (44.4%) of crystals, m.p. s 128.5, 133°–135.5°.

ANALYSIS: Calculated for $C_{19}H_{22}FNO_2$: 72.36%C; 7.03%H; 4.44%N; Found: 72.42%C; 7.07%H; 4.36%N.

(b)

trans-3-o-Fluorophenyl-4-p-methoxyphenyl-1-methyl-4-piperidinol

The chromatography fractions enriched in the trans isomer obtained from the experiment described above were combined and evaporated in vacuo to afford 0.35 g of solid. Recrystallization from cyclohexane yielded 0.15 g (7.9%) of crystalline solid, m.p. s 107, 111°–113.5°.

ANALYSIS: Calculated for $C_{19}H_{22}FNO_2$: 72.36%C; 7.03%H; 4.44%N; Found: 72.16%C; 7.00%H; 4.31%N.

EXAMPLE 18

(a)

cis-3-o-fluorophenyl-4-p-fluorophenyl-1-methyl-4-piperidinol

To a solution of 2.63 g of 4-bromofluorobenzene in 25 ml of anhydrous ether at −20° under nitrogen was added 6.82 ml of 2.2 M n-butyllithium in hexane. The resulting solution was stirred for 10 minutes at −20° and then warmed to room temperature. To this solution was added dropwise with stirring under nitrogen a solution of 12.4 g of 3-o-fluorophenyl-1-methyl-4-piperidone. The resulting solution was stirred for 3½ hours at room temperature, diluted with 50 ml of water, and extracted with ether (2×50 ml). The combined organic extracts were dried over anhydrous $Na_2SO_4$ and evaporated in vacuo to give 2.18 g of solid.

This material was chromatographed on 80 g of silica gel using acetone as eluant until the less polar trans isomer came off and then eluting with 25% MeOH/acetone. The fractions containing the more polar cis isomer (major product) were combined and evaporated in vacuo to provide 1.05 g (57.7%) of crystalline solid. Recrystallization from cyclohexane afforded 0.67 g (36.8%) of crystals, m.p. s 156, 161°–163°.

ANALYSIS: Calculated for $C_{18}H_{19}F_2NO$: 71.27%C; 6.31%H; 4.62%N; 12.53%F; Found: 71.53%C; 6.15%H; 4.57%N; 12.52%F.

(b)
trans-3-o-Fluorophenyl-4-p-fluorophenyl-1-methyl-4-piperidinol maleate

To a solution of 13.13 g of 4-bromofluorobenzene in 120 ml of dry ether at −15° under nitrogen was added 34.09 ml of 2.2 M n-butyllithium in hexane. The resulting solution was stirred for 15 minutes at −15° and then warmed to room temperature. To this solution was added dropwise with stirring under nitrogen a solution of 6.22 g of 3-o-fluorophenyl-1-methyl-4-piperidone in 60 ml of dry ether. The resulting solution was stirred for 4 hours at room temperature, diluted with 250 ml of water and extracted with ether (2×250 ml). The combined extracts were dried over anhydrous sodium sulfate and evaporated in vacuo to afford 11.38 g of solid. This material was chromatographed on 300 g silica gel using first acetone and then 25% methanol/acetone. The less polar trans isomer, which eluted with acetone, was contained in two fractions. The first of these fractions also contained some non-polar by-products. The second fraction was pure trans alcohol. This latter fraction was evaporated in vacuo to give 0.47 g (5.2%) of an oil, which crystallized on standing. This material was dissolved in 10 ml of ether and 1 ml of absolute ethanol and treated with 0.2 g of maleic acid dissolved in 5 ml of ether and 2 ml of absolute ethanol. After stirring for 15 minutes, the salt was filtered, washed with ether, and dried to give 0.41 g (3.3%) of crystalline solid, m.p. s 191, 195°–197° (with bubbling). Recrystallization from ethanol afforded 0.29 g (2.3%) of crystals, m.p. s 197, 204°–205.5° (with bubbling).

ANALYSIS: Calculated for $C_{18}H_{19}F_2NO \cdot C_4H_4O_4$: 63.00%C; 5.53%H; 3.34%N; Found: 62.82%C; 5.54%H; 3.20%N.

EXAMPLE 19 cis-1,2,3,4,4a,9b-Hexahydro-4a-(4-methoxyphenyl)-2-benzofuro[3,2-c]pyridine hydrochloride A suspension of 10.60 g of an approximately 80:20 mixture of cis-3-(2-fluorophenyl)-4-(4-methoxyphenyl)-1-methyl-4-piperidinol and 4-(5-bromo-2-methoxyphenyl)-3-(2-fluorophenyl)-1-methyl-4-piperidinol and 1.23 g of sodium hydride in 65 ml of dry benzene was heated almost to reflux under nitrogen and then 65 ml of dry dimethylformamide was added. The reaction mixture was heated at reflux for 2½ hours. The cooled reaction mixture was poured into 400 ml of water and extracted with ether (2×250 ml). The combined extracts were washed with water (3×250 ml), dried over anhydrous $Na_2SO_4$ and evaporated in vacuo to afford 10.26 g of an oil.

This material was chromatographed on 375 g of silica gel using first acetone and then 25% of MeOH/acetone as eluants. cis-1,2,3,4,4a,9b-hexahydro-4a-(4-methoxyphenyl)-2-methyl-benzofuro[3,2-c]pyridine eluted first followed by fractions enriched in cis-4a(5-bromo-2-methoxyphenyl)-1,2,3,4,4a-9b-hexahydro-2-methylbenzofuro[3,2-c]pyridine. The fractions containing the former compound were combined and evaporated in vacuo to provide 7.22 g (72.75%) of an oil.

A 2.95 g portion of this material was dissolved in 50 ml of ether and 5 ml of absolute ethanol and treated with 20 ml of ether saturated with HCl. After stirring for ¼ hour, the precipitated salt was filtered, washed with ether, and dried at 50° to afford 2.94 g (64.5%) of crystalline solid, m.p. s 262.5, 263.5°–264.5° (with bubbling). Recrystallization from ethanol gave 2.54 g (55.7%) of crystals, m.p. s 255, 258°–259.5° (with bubbling).

ANALYSIS: Calculated for $C_{19}H_{21}NO_2 \cdot HCl$: 68.77%C; 6.68H; 4.22N; Found: 68.5%C; 6.60%H; 4.12%N.

EXAMPLE 20 cis-3-o-Fluorophenyl-4-o-methoxyphenyl-1-methyl-4-piperidinol

To a solution of 23.38 g of o-bromoanisole in 200 ml of anhydrous ether at −15° under nitrogen was added 56.82 ml of 2.2 M n-butyllithium in hexane. The resulting solution was stirred for 15 minutes at −15° and then warmed to room temperature. To this solution was added dropwise with stirring under nitrogen a solution of 10.36 g of 3-o-fluorophenyl-1-methyl-4-piperidone in 100 ml of dry ether. The resultant solution was stirred for 3½ hours at room temperature, diluted with 400 ml of water, and extracted with ether (2×400 ml). The combined extracts were dried over anhydrous $Na_2SO_4$ and evaporated in vacuo to give 17.74 g of an oil. This material was chromatographed on 450 g of silica gel using first acetone and then 25% MeOH/acetone as eluant. The pure fractions were combined and evaporated in vacuo to afford 6.90 g of crystalline solid. An additional 3.82 g of material, which was product alcohol contaminated by some polar by-products, was obtained as a solid foam by further elution. Total crude yield: 10.72 g (68.0%). The 6.90 g of pure material was recrystallized from hexane to afford 5.63 g (55.5%) of crystals, m.p. s 91, 93°–94.5°.

ANALYSIS: Calculated for $C_{19}H_{22}FNO_2$: 72.36%C; 7.03%H; 4.44%N; Found: 72.11%C; 6.92%H, 4.32%N.

EXAMPLE 21 cis-1,2,3,4,4a,9b-Hexahydro-4a-(2-methoxyphenyl)-2-methyl-benzofuro[3,2-c]-pyridine A suspension of 5.05 of cis-3o-fluorophenyl-4-o-methoxyphenyl-1-methyl-4-piperidinol and 0.614 g of sodium hydride in 32 ml of dry benzene was heated almost to reflux under nitrogen, and then 32 ml of dry dimethylformamide was added. The reaction mixture was heated at reflux for 1 hour (initially considerable foaming took place, and the heating mantle had to be raised and lowered to control it). The cooled reaction mixture was poured into 200 ml of water and extracted with ether (2×125 ml). The combined extracts were washed with water (3×125 ml), dried over anhydrous $Na_2SO_4$, and evaporated in vacuo to give 4.56 g (96.5%) of crystalline solid, m.p. s 140, 147°14 150°. Recrystallization from hexane afforded 3.94 g (83.4%) of colorless crystals, m.p. s 147, 150°–151.5°.

ANALYSIS: Calculated for $C_{19}H_{21}NO_2$: 77.26%C; 7.17%H; 4.74%N; Found: 77.22%C; 7.24%H; 4.68%N.

EXAMPLE 22 cis-4a-(4-Fluorophenyl)-1,2,3,4,4a,9b-hexahydro-2-methyl-benzofuro[3,2-c]pyridine hydrochloride A suspension of 0.468 g of sodium hydride and 3.70 g of cis-3-o-fluorophenyl-4-p-fluorophenyl-1-methyl-4-piperidinol in 25 ml of dry benzene was heated almost to reflux under nitrogen and 25 ml of dry dimethylformamide was added. The reaction mixture was heated at reflux for 1 hour, diluted for 150 ml of water, and extracted with ether (2×100 ml). The combined extracts were washed with water (2×100 ml), dried over anhydrous Na₂SO₄, and evaporated in vacuo to give 3.38 g (97.8%) of an oil. This material was dissolved in 50 ml of ether and treated with 20 ml of ether saturated with HCl. After stirring for 15 minutes, the solvent was removed in vacuo. The precipitated salt was triturated with ether, filtered, and dried to afford 3.45 g (88.4%) of crystalline solid, m.p. s 233, 243°–246°. Recrystallization from ethanol/ether gave 2.58 g (66.1%) of crystalline solid, m.p. s 247, 251°–253°.

ANALYSIS: Calculated for $C_{18}H_{18}FNO \cdot HCl$: 67.60%C; 5.99%H; 4.38%N; Found: 67.51%C; 5.97%H; 4.33%N.

EXAMPLE 23

(a)

cis-3-o-Fluorophenyl-1-methyl-4-p-tolyl-4-piperidinol

To a solution of 17.10 g of 4-bromotoluene in 160 ml of dry ether at −15° under nitrogen was added 45.45 ml of 2.2 M n-butyllithium in hexane. The resulting solution was stirred for 15 minutes at −15° and then warmed to room temperature. To this solution was added dropwise with stirring under nitrogen a solution of 8.29 g of 3-o-fluorophenyl-1-methyl-4-piperidone in 80 ml of dry ether. The resulting solution was stirred for 3 hours at room temperature, diluted with 325 ml of water, and extracted with ether (2×300 ml). The combined extracts were extracted with 2N HCl (2×150 ml). The organic layer was discarded after TLC analysis. The aqueous acidic extracts were cooled to 0°, basified with 50% aqueous NaOH, and extracted with ether (2×300 ml). The combined extracts were dried over anhydrous Na₂SO₄ and evaporated in vacuo to give 11.41 g (95.3%) of crystalline solid, m.p. s 57, 65°–70°. Recrystallization from cyclohexane afforded 6.95 g (58.0%) of crystalline solid, m.p. s 132, 136°–137.5°.

ANALYSIS: Calculated for $C_{19}H_{22}FNO$: 76.22%C; 7.41%H; 4.68%N; Found: 76.34%C; 7.38%H; 4.21%N.

(b)

trans-3-o-Fluorophenyl-1-methyl-4-p-tolyl-4-piperidinol

The mother liquors obtained from the procedure described above were evaporated in vacuo and then chromatographed on 150 g of silica gel using acetone as eluant. The fractions enriched in trans alcohol were combined and evaporated in vacuo to give 2.20 g (18.4%) of crystalline solid, m.p. 97, s 107°–111°. Recrystallization from cyclohexane afforded 1.30 g (10.9%) of pure trans alcohol as crystals, m.p. s 120, 122°–123.5°.

ANALYSIS: Calculated for $C_{19}H_{22}FNO$: 76.22%C; 7.41%H; 4.68%N; Found: 76.33%C; 7.43%H; 4.56%N.

EXAMPLE 24 cis-1,2,3,4,4a,9b-Hexahydro-2-methyl-4a-(4-tolyl)-benzofuro[3,2-c]pyridine hydrochloride A suspension of 3.74 g of cis-3-o-fluorophenyl-1-methyl-4-p-tolyl-4-piperidinol and 0.48 g of sodium hydride in 25 ml of dry benzene was heated almost to reflux under nitrogen and then 25 ml of dry dimethylformamide was added. The reaction mixture was heated at reflux for 1 hour, diluted with 150 ml of water, and extracted with ether (2×100 ml). The combined extracts were washed with water (3×100 ml), dried over anhydrous Na₂SO₄, and evaporated in vacuo to give 3.29 g (94.2%) of an oil.

This material was dissolved in 50 ml of ether and treated with 20 ml of ether saturated with HCl. After stirring for 15 minutes, the salt was filtered, washed with ether, and dried to provide 3.38 g (89.6%) of crystalline solid, m.p. s 276, 278°–280° (with bubbling). Recrystallization from ethanol afforded 2.98 g (75.5%) of crystals, m.p. s 281, 284°–286° C. (with bubbling).

ANALYSIS: Calculated for $C_{19}H_{21}NO \cdot HCl$: 72.25%C; 7.02%H; 4.44%N; Found: 72.28%C; 7.04%H; 4.35%N.

EXAMPLE 25

(a)

cis-3-o-Fluorophenyl-4-m-methoxyphenyl-1-methyl-4-piperidinol

To a solution of 1.40 g of m-bromoanisole in 12.5 ml of dry tetrahydrofuran at −60° under nitrogen was added dropwise 3.41 ml of 2.2 M n-butyllithium in hexane. The resulting suspension was stirred for 2 hours at −50° to −60° after which a solution of 0.622 g of 3-o-fluorophenyl-1-methyl-4-piperidone in 7.5 ml of dry tetrahydrofuran was added dropwise with stirring. The temperature was maintained at −50° to −60° for 1 hour. The dry ice bath was then removed, and the temperature allowed to rise to room temperature. After stirring for 1½ hour at room temperature, the reaction mixture was poured into 25 ml of water and extracted with ether (2×25 ml). The combined organic layers were extracted with 2N hydrochloric acid (2×12.5 ml). The organic layer was shown by TLC to contain only non-polar by-products and was, therefore, discarded. The aqueous acidic extracts were cooled to 0° and basified with 50% aqueous NaOH and extracted with Et₂O (2×25 ml). The combined extracts were dried over anhydrous Na₂SO₄ and evaporated in vacuo to give 0.85 g (89.8%) of crystalline solid, m.p. s 105, 119°–122°. Recrystallization from cyclohexane afforded 0.62 g (65.5%) of crystalline solid, m.p. s 125, 131.5°–132.5°.

ANALYSIS: Calculated for $C_{19}H_{22}FNO_2$: 72.36%C; 7.03%H; 4.44%N; Found: 72.53%C; 7.03%H; 4.16%N.

(b)

trans-3-o-Fluorophenyl-4-m-methoxyphenyl-1-methyl-4-piperidinol

To a solution of 14.03 g of m-bromoanisole in 120 ml of dry tetrahydrofuran at −60° under nitrogen was added dropwise with stirring over 10 minutes 34.1 ml of 2.2 M n-butyllithium in hexane. The resulting suspension was stirred for 2 hours at −50° to −60° after which a solution of 6.22 g of 3-o-fluorophenyl-1-methyl-4-piperidone in 60 ml of dry tetrahydrofuran was added dropwise with stirring. The temperature was maintained at −50° to −60° for 1 hour. The dry ice bath was removed, and the temperature was allowed to rise to room temperature. After stirring at room temperature for 2 hours, the reaction mixture was diluted with 250 ml of water and extracted with ether (2×250 ml). The combined organic layers were extracted with 2N HCl (2×125 ml). The organic layer was shown by TLC to contain only non-polar by-products and was, therefore, discarded.

The aqueous acidic extracts were cooled to 0°, basified with 50% aqueous NaOH and extracted with dichloromethane (2×250 ml). The combined extracts were dried over anhydrous Na₂SO₄ and evaporated in vacuo to afford 9.25 g (97.8%) of crystalline solid, m.p. s 105, 124°–128°. Recrystallization from cyclohexane gave 7.32 g (77.4%) of pure cis alcohol as a crystalline solid, m.p. s 125, 131°–132.5°.

The mother liquors from the recrystallization were combined with those from the other smaller experiment described above (0.003 mole scale) to provide 1.74 g of a gum. This material was chromatographed on 65 g silica gel using acetone as eluant. The fractions enriched the less polar trans alcohol were combined and evaporated in vacuo to give 0.52 g (5.0%) of an an oil which crystallized on standing. Recrystallization from isopropanol afforded 0.20 g (1.9%) of crystals, m.p. s 130, 140°–141°.

ANALYSIS: Calculated for $C_{19}H_{22}FNO_2$: 72.36%C; 7.03%H; 4.44%N; Found: 72.29%C; 6.63%H; 4.40%N.

EXAMPLE 26 cis-1,2,3,4,4a,9b-Hexahydro-4a-(3-methoxyphenyl)-2-methyl-benzofuro-[3,2-c]pyridine hydrochloride A suspension of 7.41 g of cis-3-o-fluorophenyl-4-m-methoxyphenyl-1-methyl-4-piperidinol and 0.90 g of sodium hydride in 47 ml of dry benzene was heated almost to reflux under nitrogen and then 47 ml of dry dimethylformamide was added. The reaction mixture was heated at reflux for 1 hour, diluted with 300 ml of water and extracted with ether (2×200 ml). The combined extracts were washed with water (3×200 ml), dried over anhydrous $Na_2SO_4$, and evaporated in vacuo to afford 7.37 g (100+%) of an oil.

A 2.95 g portion of this material was dissolved in 50 ml of ether and treated with 20 ml of ether saturated with hydrogen chloride. After stirring for 15 minutes, the precipitated salt was filtered, washed with ether, and dried to provide 3.00 g (90.4%) of crystalline solid, m.p. s 247, 250°–254° (with bubbling). Recrystallization from ethanol gave 2.54 g (76.5%) of crystals, m.p. s 247, 251°–253° (with bubbling).

ANALYSIS: Calculated for $C_{19}H_{21}NO_2.HCl$: 68.77%C; 6.68%H; 4.22%N; Found: 68.90%C; 6.79%H; 4.16%N.

EXAMPLE 27

(a)

cis-3-o-Fluorophenyl-1-methyl-4-m-tolyl-4-piperidinol

To a solution of 10.69 g of m-bromotoluene in 100 ml of dry tetrahydrofuran at −60° under nitrogen was added dropwise with stirring over 10 minutes 28.41 ml of 2.2 M n-butyllithium in hexane. The resulting suspension was stirred for 2 hours at −50° to −60° after which a solution of 5.18 g of 3-o-fluorophenyl-1-methyl-4-piperidone in 50 ml of dry tetrahydrofuran was added dropwise with stirring. The temperature was maintained at −50° to −60° for 1 hour. The dry ice bath was removed, and the temperature was allowed to rise to room temperature. After stirring at room temperature for 2 hours, the reaction mixture was diluted with 200 ml of water and extracted with ether (2×200 ml). The combined organic layers were extracted with 2N HCl (2×100 ml). The organic layer was shown by TLC to contain only non-polar by-products and was, therefore, discarded.

The aqueous acidic extracts were cooled to 0°, basified with 50% aqueous NaOH, and extracted with dichloromethane (2×200 ml). The combined extracts were dried over anhydrous $Na_2SO_4$ and evaporated in vacuo to give 7.62 g (100+%) of crystalline solid, m.p. s 100, 130°–136°. Recrystallization from cyclohexane afforded 4.92 g (65.7%) of colorless crystalline solid, m.p. s 142, 146°–148°.

ANALYSIS: Calculated for $C_{19}H_{22}FNO$: 76.22%C; 7.41%H; 4.68%N; Found: 76.20%C; 7.55%H; 4.51%N.

(b)

trans-3-o-Fluorophenyl-1-methyl-4-m-tolyl-4-piperidinol

The mother liquors obtained from the procedure described above were chromatographed on 45 g of silica gel using acetone as eluant. The fractions enriched in the trans alcohol (which eluted first) were combined and evaporated in vacuo to afford 0.46 g (6.1%) of an oil. A 0.37 g portion of the above material was dissolved in 10 ml of ether and 1 ml of absolute ethanol and treated with a solution of 0.18 g of maleic acid dissolved in 5 ml of ether and 2 ml of absolute ethanol. After the addition was complete, crystallization started very slowly. The mixture was stirred for 15 minutes and then allowed to stand overnight at room temperature. After cooling to 0° the precipitated salt was filtered, washed with ether, and dried to afford 0.26 g (3.1%) of crystals, m.p. s 136, 138°–140°.

ANALYSIS: Calculated for $C_{19}H_{22}FNO.C_4H_4O_4$: 66.49%C; 6.31%H; 3.37%N; Found: 66.17%C; 6.26%H; 3.33%N.

EXAMPLE 28 cis-1,2,3,4,4a,9b-Hexahydro-2-methyl-4a-(3-tolyl)-benzofuro[3,2-c]pyridine hydrochloride A suspension of 4.49 g of cis-3-o-fluorophenyl-1-methyl-4-m-tolyl-4-piperidinol and 0.576 g of sodium hydride in 30 ml of dry benzene was heated almost to reflux under nitrogen and then 30 ml of dry dimethylformamide was added. The reaction mixture was heated at reflux for 7 hours, diluted with 175 ml of water, and extracted with ether (2×125 ml). The combined extracts were dried over anhydrous $Na_2SO_4$ and evaporated in vacuo to give 4.25 g (100+%) of an oil.

This material was dissolved in 60 ml of ether and treated with 25 ml of ether saturated with HCl. After stirring for 30 minutes, the precipitated salt was filtered, washed with ether, and dried to provide 4.31 g (91.0%) of crystalline solid, m.p. s 259, 275°–278° (with bubbling). Recrystallization from ethanol afforded 3.92 g (82.7%) of colorless crystals, m.p. s 269, 279°–281.5° (with bubbling).

ANALYSIS: Calculated for $C_{19}H_{21}NO.HCl$: 72.25%C; 7.02%H; 4.44%N; Found: 72.07%; 7.23%H; 4.35%N.

EXAMPLE 29 cis-4-o-Chlorophenyl-3-o-fluorophenyl-1-methyl-4-piperidinol

To a solution of 1.44 g of 2-bromochlorobenzene in 12.5 ml of dry tetrahydrofuran at −60° under nitrogen was added dropwise with stirring over 5 minutes 3.41 ml of 2.2 M n-butyllithium in hexane. The resulting solution was stirred for 2 hours at −60° after which a solution of 0.622 g of 3-o-fluorophenyl-1-methyl-4-piperidone in 7.5 ml of dry tetrahydrofuran was added dropwise with stirring. The temperature was maintained at −60° for 1 hour. The dry ice bath was removed, and the temperature was allowed to rise to room temperature. After stirring for 2 hours at room temperature, the reaction mixture was diluted with 25 ml of water and extracted with ether (2×25 ml). The combined organic layers were extracted with 2N HCl (2×12.5 ml). The organic layer was shown by TLC to contain only non-polar by-products and was, therefore, discarded.

The aqueous acidic extracts were cooled to 0°, basified with 50% aqueous NaOH, and extracted with dichloromethane (2×25 ml). The combined extracts were dried over anhydrous $Na_2SO_4$ and evaporated in vacuo to afford 0.81 g (84.4%) of solid. Recrystallization from cyclohexane gave 0.22 g (22.9%) of crystalline solid, mp. s 115, 123°–125°.

ANALYSIS: Calculated for $C_{18}H_{19}ClFNO$: 67.60%C; 5.99%H; 4.38%N; Found: 67.61%C; 5.94%H; 4.31%N.

EXAMPLE 30 cis-4a-(2-Chlorophenyl)-1,2,3,4,4a,9b-hexahydro-2-methyl-benzofuro[3,2-c]-pyridine hydrochloride A suspension of 1.92 g of cis-4-o-chlorophenyl-3-o-fluorophenyl-1-methyl-4-piperidinol and 0.23 g of sodium hydride in 12 ml of dry benzene was heated almost to reflux under nitrogen and then 12 ml of dry dimethylformamide was added. The resulting mixture was heated at reflux for 1 hour, diluted with 75 ml of water, and extracted with ether (2×50 ml). The combined extracts were washed with water (3×50 ml), dried over anhydrous $Na_2SO_4$, and evaporated in vacuo to give 1.50 g (83.4%) of a gum.

This material was dissolved in 30 ml of ether and treated with 15 ml of ether saturated with HCl. After stirring for 30 minutes, the precipitated salt was filtered, washed with ether, and dried to provide 1.51 g (74.8%) of crystalline solid. Recrystallization from isopropanol afforded 1.08 g (53.5%) of crystalline solid, m.p. s 250, 258°–259.5°.

ANALYSIS: Calculated for $C_{18}N_{18}ClNO\cdot HCl$: 64.29%C; 5.70%H; 4.17%N; Found: 63.89%C; 5.73%H; 3.97%N.

EXAMPLE 31 cis-3-o-Fluorophenyl-1-methyl-4-o-tolyl-4-piperidinol

To a solution of 12.83 g of 2-bromotoluene in 120 ml of dry tetrahydrofuran at −60° under nitrogen was added dropwise over 20 minutes 34.1 ml of 2.2 M n-butyllithium in hexane. The resulting suspension was stirred for 2 hours at −50° to −60° after which a solution of 6.22 g of 3-o-fluorophenyl-1-methyl-4-piperidone in 60 ml of dry tetrahydrofuran was added dropwise with stirring. The temperature was maintained at −50° to −60° for ½ hour, allowed to warm to room temperature, and then stirred at room temperature overnight.

The reaction mixture was poured into 250 ml of water and extracted with ether (2×250 ml). The combined organic layers were extracted with 2N HCl (2×125 ml). The organic layer was shown by TLC to contain only non-polar by-products and was, therefore, discarded.

The aqueous acidic extracts were cooled to 0°, basified with 50% aqueous NaOH, and extracted with dichloromethane (2×250 ml). The combined extracts were dried over anhydrous $Na_2SO_4$ and evaporated in vacuo to provide 8.51 g (94.8%) of crystalline solid. Recrystallization from cyclohexane afforded 5.98 g (66.6%) of crystals, m.p. s 121, 143°–144.5°.

ANALYSIS: Calculated for $C_{19}H_{22}FNO$: 76.22%C; 7.41%H; 4.68%N; Found: 76.13%C; 7.43%H; 4.68%N.

EXAMPLE 32 cis-1,2,3,4,4a,9b-Hexahydro-4a-(4-hydroxyphenyl)-2-methyl-benzofuro[3,2-c]-pyridine A mixture of 3.46 g of cis-1,2,3,4,4a,9b-hexahydro-4a-(4-methoxyphenyl)-2-methyl-benzofuro[3,2-c]pyridine and 3.57 g of lithium thiomethoxide in 30 ml of dry hexamethylphosphoramide was heated under a drying tube at 140° for 4½ hours. The reaction mixture was diluted with 350 ml of water, and the pH was adjusted to 7 by slow addition of 2N HCl with stirring. As the pH reached neutral, the product precipitated out. The mixture was cooled to 0° and stirred for 30 minutes. The precipitated material was filtered, washed with water and then with a small amount of ether, and dried to give 2.77 g (84.2%) of crystalline solid, m.p. s 209, 215°–217°. Recrystallization from ethanol afforded 2.33 g (70.8%) of crystals, m.p. s 215, 222°–224°.

ANALYSIS: Calculated for $C_{18}H_{19}NO_2$: 76.84%C; 6.81%H; 4.98%N; Found: 76.67%C; 6.90%H; 4.95%N.

EXAMPLE 33

(a)

cis-3-o-fluorophenyl-4-m-fluorophenyl-1-methyl-4-piperidinol

To a solution of 13.13 g of 3-bromofluorobenzene in 120 ml of dry tetrahydrofuran at −60° under nitrogen was added dropwise with stirring over 20 minutes 34.1 ml of 2.2 M n-butyllithium in hexane. The resulting solution was stirred for 2 hours at −50° to −60° after which a solution of 6.22 g of 3-o-fluorophenyl-1-methyl-4-piperidone in 60 ml of dry tetrahydrofuran was added. The reaction mixture was stirred for 45 minutes at −50° to −60° and then poured into 250 ml of water and extracted with ether (2×250 ml). The combined organic layers were extracted with 2N HCl (2×125 ml). The organic layer was shown by TLC to contain only non-polar by-products and was, therefore, discarded.

The aqueous acidic extracts were cooled to 0°, basified with 50% aqueous NaOH, and extracted with dichloromethane (2×250 ml). The combined extracts were dried over anhydrous $Na_2SO_4$ and evaporated in vacuo to afford 8.55 g (94.0%) of crystalline solid. Recrystallization from cyclohexane gave 7.35 g (80.8%) of crystalline solid, m.p. s 167, 174°–175.5°.

ANALYSIS: Calculated for $C_{18}H_{19}F_2NO$: 71.27%C; 6.31%H; 4.62%N; Found: 71.39%C; 6.41%H; 4.38%N.

(b)

trans-3-o-Fluorophenyl-4-m-fluorophenyl-1-methyl-4-piperidinol maleate

The mother liquors obtained from the procedure described above were chromatographed on 40 g of silica gel using acetone as eluant. The fractions enriched in trans alcohol were combined and evaporated in vacuo to give 0.34 g (3.7%) of a gum. This material was dissolved in 10 ml of ether and 1 ml of absolute ethanol and treated with 0.15 g of maleic acid dissolved in 5 ml of ether and 1.5 ml of absolute ethanol. The salt did not crystallize out right away. After stirring for 1 hour a small amount of the material was cooled and scratched whereupon crystallization occurred. This material was used to seed the rest of the mixture. After 30 minutes of additional stirring, the mixture was cooled, filtered, washed with ether, and dried to afford 0.27 g (2.1%) of crystalline solid, m.p. s 168, 171.5°–173° (with bubbling).

ANALYSIS: Calculated for $C_{18}H_{19}F_2NO \cdot C_4H_4O_4$: 63.00%C; 5.53%H; 3.34%N; Found: 63.03%C; 5.61%H; 3.24%N.

EXAMPLE 34 cis-1,2,3,4,4a,9b-Hexahydro-2-methyl-4a-(2-tolyl)-benzofuro[3,2-c]pyridine hydrochloride A suspension of 3.59 g of cis-3-o-fluorophenyl-1-methyl-4-o-tolyl-4-piperidinol and 0.461 g of sodium hydride in 24 ml of dry benzene was heated almost to reflux under nitrogen and then 24 ml of dry dimethylformamide was added. The reaction mixture was heated at reflux for 1 hour, diluted with 150 ml of water, and extracted with ether (2×100 ml). The combined extracts were washed with water (3×100 ml), dried over anhydrous $Na_2SO_4$, and evaporated in vacuo to afford 3.00 g (89.5%) of a gum.

This material was dissolved in 50 ml of ether and treated with 20 ml of ether saturated with HCl. After stirring for 30 minutes, the precipitated salt was filtered, washed with ether, and dried to give 3.03 g (79.9%) of crystalline solid, m.p. s~170, 233°-240° (with bubbling). Recrystallization from isopropanol afforded 2.16 g (57.0%) of crystals, m.p. s 258, 262.5°-264° (with bubbling).

ANALYSIS: Calculated for $C_{19}H_{21}NO \cdot HCl$: 72.25%C; 7.02%H; 4.44%N; Found: 71.94%C; 6.97%H; 4.34%N.

EXAMPLE 35 cis-4a-(3-Fluorophenyl)-1,2,3,4,4a,9b-hexahydro-2-methyl-benzofuro[3,2-c]pyridine hydrochloride A mixture of 6.37 g of cis-3-o-fluorophenyl-4-m-fluorophenyl-1-methyl-4-piperidinol and 0.81 g of sodium hydride in 42 ml of dry benzene was heated almost to reflux under nitrogen and then 42 ml of dry dimethylformamide was added. The resulting mixture was heated at reflux for 1 hour, diluted with 275 ml of water, and extracted with ether (2×175 ml). The combined extracts were washed with water (3×175 ml), dried over anhydrous $Na_2SO_4$, and evaporated in vacuo to provide 6.02 g (100+%) of an oil.

This material was dissolved in 100 ml of dry ether and treated with 35 ml of ether saturated with HCl. After stirring for 15 minutes, the precipitated salt was filtered, washed with ether, and dried to afford 6.20 g (92.3%) of crystalline solid, m.p. s 255, 262°-267° (with bubbling). Recrystallization from ethanol gave 5.36 g (79.8%) of crystals, m.p. s 267, 274°-276° (with bubbling).

ANALYSIS: Calculated for $C_{18}H_{18}FNO \cdot HCl$: 67.60%C; 5.99%H; 4.38%N; Found: 67.54%C; 6.10%H; 4.26%N.

EXAMPLE 36

(a)
cis-4-p-Chlorophenyl-3-o-fluorophenyl-1-methyl-4-piperidinol

To a solution of 14.36 g of 4-bromochlorobenzene in 120 ml of dry tetrahydrofuran was added dropwise with stirring at −60° under nitrogen 34.1 ml of 2.2 M n-butyllithium in hexane. The resulting suspension was stirred for 2 hours at −60° after which a solution of 6.22 g of 3-o-fluorophenyl-1-methyl-4-piperidone in 60 ml of dry tetrahydrofuran was added dropwise with stirring maintaining the temperature between −50° and −60°. After the addition was complete, the temperature was maintained at −50° to −60° for 1 hour and then warmed to room temperature. The reaction mixture was stirred at room temperature for 1 hour, diluted with 250 ml of water, and extracted with ether (2×250 ml). The combined organic layers were extracted with 2N HCl (2×125 ml). The organic layer was shown by TLC to contain only non-polar by-products and was, therefore, discarded.

The aqueous acidic extracts were cooled to 0°, basified with 50% aqueous NaOH, and extracted with dichloromethane (2×250 ml). The combined extracts were dried over anhydrous $Na_2SO_4$ and evaporated in vacuo to afford 8.95 g (93.3%) of crystalline solid. Recrystallization from cyclohexane gave 6.35 g (66.2%) of crystals, m.p. s 150, 158°-160°.

ANALYSIS: Calculated for $C_{18}H_{19}ClFNO$: 67.60%C; 5.99%H; 4.38%N; Found: 67.53%C; 5.99%H; 4.29%N.

(b)
trans-4-p-Chlorophenyl-3-o-fluorophenyl-1-methyl-4-piperidinol maleate

The mother liquors obtained from the procedure described above were chromatographed on 40 g of silica gel using acetone as eluant. The fractions enriched in the trans alcohol (which eluted before the cis alcohol) were combined and evaporated in vacuo to give 0.28 g (2.9%) of an oil. This material was dissolved in 10 ml of ether and 1 ml of absolute ethanol and treated with a solution of 0.12 g of maleic acid dissolved in 5 ml of ether and 1 ml of absolute ethanol. After the addition was complete, the mixture was stirred for 1 hour and filtered. The precipitated salt was washed with ether and dried to afford 0.26 g (2.0%) of crystalline solid, m.p. s 200, 202°-203° (with bubbling).

ANALYSIS: Calculated for $C_{18}H_{19}ClFNO \cdot C_4H_4O_4$: 60.62%C; 5.32%H; 3.21%N; Found: 60.42%C; 5.54%H; 3.08%N.

EXAMPLE 37 cis-4a-(4-Chlorophenyl)-1,2,3,4,4a,9b-hexahydro-2-methyl-benzofuro[3,2-c]-pyridine hydrochloride A mixture of 4.00 g of cis-4-p-chlorophenyl-3-o-fluorophenyl-1-methyl-4-piperidinol and 0.48 g of sodium hydride in 25 ml of dry benzene was heated almost to reflux under nitrogen and then 25 ml of dry dimethylformamide was added. The resulting mixture was heated at reflux for 1 hour. The cooled reaction mixture was diluted with 150 ml of water and extracted with ether (2×100 ml). The combined extracts were washed with water (3×100 ml), dried over anhydrous $Na_2SO_4$, and evaporated in vacuo to provide 3.78 g of an oil.

This material was dissolved in 50 ml of ether and treated with 20 ml of ether saturated with HCl. After stirring for 15 minutes the precipitated salt was filtered, washed with ether, and dried to give 3.87 g (92.1%) of crystalline solid, m.p. s 272, 277.5°-281° (with bubbling). Recrystallization from ethanol afforded 3.46 g (82.3%) of crystals, m.p. s 275, 282°-284° (with bubbling).

ANALYSIS: Calculated for $C_{18}H_{18}ClNO \cdot HCl$: 64.29%C; 5.70%H; 4.17%N; Found: 64.34%C; 5.70%H; 4.16%N.

EXAMPLE 38 cis-3-o-Fluorophenyl-4-(2-furyl)-1-methyl-4-piperidinol

To a solution of 5.11 g of furan in 120 ml of dry tetrahydrofuran at −25° under nitrogen was added dropwise with stirring over 30 minutes 34.1 ml of 2.2 M n-butyllithium in hexane. The resulting solution was stirred for 2 hours at −10° to −15° after which a solution of 6.22 g of 3-o-fluorophenyl-1-methyl-4-piperidone in 60 ml of dry tetrahydrofuran was added dropwise at −15°. The bath was removed and the mixture allowed to gradually warm to room temperature. After stirring for 2 hours at room temperature, the reaction mixture was diluted with 250 ml of water and extracted with ether (2×250 ml). The combined organic layers were washed with water (2×250 ml), dried over anhydrous $Na_2SO_4$, and evaporated in vacuo to give 8.37 g of solid. Recrystallization from cyclohexane afforded 6.61 g (80.0%) of crystals, m.p. s 120, 134.5°–137°.

ANALYSIS: Calculated for $C_{16}H_{18}FNO_2$: 69.80%C; 6.59%H; 5.09%N; Found: 69.85%C; 6.59%H; 4.97%N.

EXAMPLE 39 cis-4a-(3-Fluorophenyl)-1,2,3,4,4a,9b-hexahydro-benzofuro[3,2-c]pyridine maleate To a stirred solution of 2.77 g of cis-4a-(3-fluorophenyl)-1,2,3,4,4a,9b-hexahydro-2-methyl-benzofuro[3,2-c]pyridine in 25 ml of dry benzene were added 2.03 g of anhydrous $K_2CO_3$ and 1.59 g of ethyl chloroformate. The resulting mixture was heated at reflux under nitrogen for 23½ hours. The cooled reaction mixture was poured into 50 ml of water and extracted with ether (2×50 ml). The combined extracts were washed with 2N HCl (2×10 ml) of brine, dried over anhydrous $Na_2SO_4$, and evaporated in vacuo to give 3.05 g (91.4%) of the ethyl carbamate as an oil.

A mixture of 3.04 g of cis-2-ethoxycarbonyl-4a-(3-fluorophenyl)-1,2,3,4,4a,9b-hexahydro-benzofuro[3,2-c]pyridine from above, 36 ml of absolute ethanol, and 24 ml of 20% aqueous NaOH solution, was heated at reflux under nitrogen for 29 hours. Most of the ethanol was removed in vacuo. The residue was diluted with 50 ml of water and extracted with dichloromethane (2×60 ml). The combined extracts were dried over anhydrous $Na_2SO_4$ and evaporated in vacuo to provide 2.48 g of an oil.

This material was dissolved in 50 ml of ether and treated with a solution of 1.16 g of maleic acid dissolved in 15 ml of ether and 5 ml of absolute ethanol. After the addition was complete, the mixture was stirred at room temperature for 20 minutes. The precipitated salt was filtered, washed with ether and dried to afford 2.74 g (79.9%) of crystalline solid, m.p. s 157, 158.5°–160° (with bubbling). Recrystallizatin from ethanol gave 2.19 g (63.9%) of crystalline solid, m.p. s 157, 158.5°–160° (with bubbling.

ANALYSIS: Calculated for $C_{17}H_{16}FNO.C_4H_4O_4$: 65.44%C; 5.23%H; 3.63%N; Found: 65.22%C; 5.23%H; 3.58%N.

EXAMPLE 40 cis-4a-(2-Furyl)-1,2,3,4,4a,9b-hexahydro-2-methyl-benzofuro[3,2-c]pyridine hydrochloride A mixture of 4.96 g of cis-3-o-fluorophenyl-4-(2-furyl)-1-methyl-4-piperidinol and 0.69 g of sodium hydride in 36 ml of dry benzene was heated almost to reflux under nitrogen and then 36 ml of dry dimethylformamide was added. The resulting mixture was heated at reflux for 2½ hours. The cooled reaction mixture was diluted with 225 ml of water and extracted with ether (2×150 ml). The combined extracts were washed with water (3×150ml), dried over anhydrous $Na_2SO_4$, and evaporated in vacuo to afford 4.65 g of an oil which was shown by TLC to be an approximately 60:40 mixture of product/unreacted alcohol.

This material was chromatographed on 175 g of silica gel using first acetone and then 25% MeOH/acetone as eluants. The fractions enriched in cyclized material were combined and evaporated in vacuo to give 2.69 g (58.5%) of an oil. In addition, some unreacted alcohol was obtained. The cyclized product was dissolved in 50 ml of ether and treated with 15 ml of ether saturated with HCl. After stirring for 15 minutes, the precipitated salt was filtered, washed with ether, and dried to afford 2.92 g (55.6%) of crystalline solid, m.p. s 206, 208°–209.5°. Recrystallization from ethanol gave 2.46 g (46.8%) of crystals, m.p. s 212, 213.5°–214°.

ANALYSIS: Calculated for $C_{16}H_{17}NO_2.HCl$: 69.86%C; 6.22%H; 4.80%N; Found: 65.82%C; 6.19%H; 4.58%N.

EXAMPLE 41 cis-1,2,3,4,4a,9b-Hexahydro-4a-(3-hydroxyphenyl)-2-methyl-benzofuro[3,2-c]pyridine A mixture of 3.50 g of cis-1,2,3,4,4a,9b-hexahydro-4a-(3-methyoxyphenyl)-2-methyl-benzofuro[3,2-c]pyridine and 3.62 g of lithium thiomethoxide in 30 ml of dry hexamethylphosphoramide was treated at 140° under a drying tube for 4½ hours. The cooled reaction mixture was diluted with 350 ml of water and the pH adjusted to 7 by slow addition of 2N HCl with stirring. The mixture was extracted with ether (2×300), and the combined extracts were washed with water (3×300 ml), dried over anhydrous $Na_2SO_4$, and evaporated in vacuo to provide 3.16 g (94.8%) a solid foam. This material was boiled and triturated with a small amount of ether. After cooling to 0°, the resulting soild was filtered off, washed with cold ether, and dried to afford 2.58 g (77.4%) of crystalline solid, m.p. s 157, 158°–160°.

ANALYSIS: Calculated for $C_{18}H_{19}NO_2$: 76.84%C; 6.81%H; 4.98%N; Found: 76.42%C; 6.83%H; 4.90%N.

EXAMPLE 42

(a)

cis-4-m-Chlorophenyl-3-o-fluorophenyl-1-methyl-4-piperidinol

To a solution of 14.36 g of 3-bromochlorobenzene in 120 ml of dry tetrahydrofuran at −60° under nitrogen was added dropwise with stirring over 20 minutes 34.1 ml of 2.2 M n-butyllithium in hexane. The resulting suspension was stirred for 2 hours at −60° after which a solution of 6.22 g of 3-o-fluorophenyl-methyl-4-piperidone in 60 ml of dry tetrahydrofuran was added dropwise with stirring. The reaction mixture was stirred for 2 hours at −50° to −60° and then warmed to −40° and poured into 250 ml of water. The mixture was extracted with ether (2×250 ml), and the combined organic layers were extracted with 2N HCl (2×125 ml). The residual organic layer was shown by TLC to contain only non-polar by-products and was, therefore, discarded.

The aqueous acidic extracts were cooled to 0°, basified with 50% aqueous sodium hydroxide, and extracted with dichloromethane (2×250 ml). The combined extracts were dried over anhydrous $Na_2SO_4$ and evaporated in vacuo to give 8.78 g (91.5%) of crystalline solid. Recrystallization from cyclohexane (with hot filtration to remove insoluble material followed by boiling down solvent until crystals started to appear) afforded 5.96 g (62.1%) of crystalline solid, m.p. s 167, 171.5°–173°.

ANALYSIS: Calculated for $C_{18}H_{19}ClFNO$: 67.60%C; 5.99%H; 4.38%N; Found: 67.47%C; 5.77%H; 4.37%N.

(b)
trans-4-m-Chlorophenyl-3-o-fluorophenyl-1-methyl-4-piperidinol maleate

The mother liquors obtained from the recrystallization described above were evaporated in vacuo to afford 1.26 g of a gum which was chromatographed on 45 g of silica gel using acetone as an eluant. The fraction enriched in trans alcohol were combined and evaporated in vacuo to give 0.58 g (6.0%) of a gum, which was mainly trans alcohol but also contained some non-polar by-product. This gum was dissolved in 15 ml of ether and treated with a solution of 0.18 g of maleic acid in 5 ml of ether and 2 ml of absolute ethanol. After 2 hours of stirring and overnight standing, the precipitated salt was filtered, washed with ether, and dried to afford 0.21 g (1.6%) of crystalline solid m.p. s 159, 162°–163.5° (with slight bubbling).

ANALYSIS: Calculated for $C_{18}H_{19}ClFNO \cdot C_4H_4O_4$: 5.32%C; 5.32%H; 3.21%N; Found: 60.89%C; 5.42%H; 3.30%N.

EXAMPLE 43 cis-4a-(3-Chlorophenyl)-1,2,3,4,4a,9b-hexahydro-2-methyl-benzofuro[3,2-c]-pyridine hydrochloride A suspension of 3.52 g of cis-4-m-chlorophenyl-3-o-fluorophenyl-1-methyl-4-piperidinol and 0.42 g of sodium hydride in 22 ml of dry benzene was heated almost to reflux under nitrogen and then 22 ml of dry dimethylformamide was added. The resulting mixture was heated to reflux for 1 hour. The cooled reaction mixture was diluted with 150 ml of water and extracted with ether (2×100 ml). The combined extracts were washed with water (3×100 ml), dried over anhydrous $Na_2SO_4$, and evaporated in vacuo to afford 3.40 g of an oil.

This material was dissolved in 50 ml of ether and treated with 15 ml of ether saturated with HCl. After stirring for 15 minutes, the precipitated salt was filtered, washed with ether, and dried to give 3.49 g (94.4%) of crystalline solid, m.p. s 250, 264°–268° (with slight bubbling). Recrystallization from ethanol afforded 3.08 g (83.3%) of crystals, m.p. s 262, 273°–275° (with slight bubbling).

ANALYSIS: Calculated for $C_{18}H_{18}ClNO \cdot HCl$: 64.29%C; 5.70%H; 4.17%N; Found: 64.42%C; 5.63%H; 4.14%N.

EXAMPLE 44 cis-3,4-Bis(o-fluorophenyl)-1-methyl-4-piperidinol

To a solution of 13.13 g of o-bromofluorobenzene in 120 ml of dry tetrahydrofuran at −60° under nitrogen was added dropwise with stirring over 30 minutes 34.1 ml of 2.2 M n-butyllithium in hexane. The resulting solution was stirred between −65° and −60° for 2 hours after which a solution of 6.22 g of 3-o-fluorophenyl-1-methyl-4-piperidone in 60 ml of dry tetrahydrofuran was added dropwise with stirring maintaining the temperature below −60°. The reaction mixture was stirred for 2 hours at −65° to −60° and then poured into 250 ml of water and extracted with ether (2×250 ml). The combined organic layers were extracted with 2N HCl (2×125 ml). The residual organic layer was shown by TLC to contain only non-polar by-products and was, therefore, discarded.

The aqueous acidic extracts were cooled to 0°, basified with 50% aqueous NaOH, and extracted with dichloromethane (2×250 ml). The combined extracts were dried over anhydrous $Na_2SO_4$ and evaporated in vacuo to give 9.06 g (99.6%) of crystalline solid. Recrystallization from cyclohexane afforded 6.88 g (75.6%) of crystalline solid, m.p. s 153, 155°–157°.

ANALYSIS: Calculated for $C_{18}H_{19}F_2NO$: 71.27%C; 6.31%H; 4.62%N; Found: 71.03%C; 6.31%H; 4.56%N.

EXAMPLE 45 cis-1,2,3,4,4a,9b-Hexahydro-4a-(2-hydroxyphenyl)-2-methyl-benzofuro[3,2-c]-pyridine A mixture of 1.51 g of cis-1,2,3,4,4a,9b-hexahydro-4a-(2-methoxyphenyl)-2-methyl-benzofuro[3,2-c]pyridine and 1.56 g of lithium thiomethoxide in 13 ml of dry hexamethylphosphoramide was heated at 140° under a drying tube for 4 hours. The cooled reaction mixture was diluted with 150 ml of water and the pH adjusted to 7 by slow addition of 2 N HCl with stirring. As the pH reached neutral, product started to precipitate out. The mixture was cooled to 0° and stirred for 30 minutes. The precipitated material was collected, washed with water and then a small amount of ether, and dried to afford 1.14 g (79.5%) of crystalline solid, m.p. s 178, 188°–191°. Recrystallization from ethanol gave 0.90 g (62.7%) of colorless crystals, m.p. s 197, 197.5°–199°.

ANALYSIS: Calculated for $C_{18}H_{19}NO_2$: 76.84%C; 6.81%H; 4.98%N; Found: 76.78%C; 6.71%H; 4.96%N.

EXAMPLE 46 cis-4a-(2-Fluorophenyl)-1,2,3,4,4a,9b-hexahydro-2-methyl-benzofuro[3,2-c]pyridine hydrochloride A suspension of 4.40 g of cis-3,4-bis(o-fluorophenyl)-1-methyl-4-piperidinol and 0.56 g of sodium hydride in 29 ml of dry benzene was heated almost to reflux under nitrogen and then 29 ml of dry dimethylformamide was added. The resulting mixture was heated at reflux for 1 hour. The cooled reaction mixture was diluted with 175 ml of water and extracted with ether (2×125 ml). The combined extracts were washed with water (3×125 ml), dried over anhydrous $Na_2SO_4$, and evaporated in vacuo to afford 4.12 g (100%) of an oil.

This material was dissolved in 60 ml of ether and treated with 20 ml of ether saturated with HCl. After stirring for 30 minutes, the precipitated salt was filtered, washed with ether, and dried to give 4.27 g (92.1%) of crystalline solid, m.p. s 235, 242°–244° (with slight bubbling). Recrystallization from isopropanol afforded 3.88 g (83.7%) of crystalline solid, m.p. s 242, 245°–247° (with slight bubbling).

ANALYSIS: Calculated for $C_{18}H_{18}FNO \cdot HCl$: 67.60%C; 5.99%H; 4.38%N; Found: 67.43%C; 5.94%H; 4.20%N.

I claim:
1. A compound of the formula

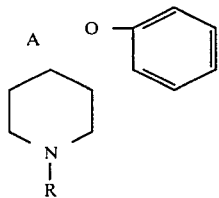

wherein A is

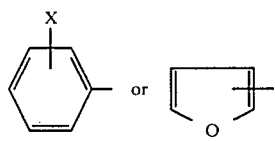

X being hydrogen, halogen, methyl, methoxy or hydroxyl, halogen being fluorine, chlorine, bromine or iodine; and R is ethyoxycarbonyl, cyanoloweralkyl, phenylcarbonylloweralkyl, phenoxyloweralkyl, phenylacetyl or cycloalkylcarbonyl where the carbonyl group of the phenylcarbonylloweralkyl may be in the ethylene ketal form; and the phenyl or phenoxy group in said phenylcarbonylloweralkyl, phenoxyloweralkyl or phenylacetyl group may have a halogen attached thereto and a pharmaceutically acceptable acid addition salt of any of the foregoing.

2. A compound as defined in claim 1 wherein R is ethoxycarbonyl.

3. A compound as defined in claim 1 wherein R is cyclopropylcarbonyl.

4. A compound as defined in claim 1 wherein R is phenylacetyl.

5. A compound as defined in claim 1 wherein R is 3-phenoxypropyl.

6. A compound as defined in claim 1 wherein R is cyanomethyl.

7. A compound as defined in claim 1 wherein R is 3-(4-fluorobenzoyl)propyl.

8. A compound as defined in claim 1 wherein R is 2-cyanoethyl.

9. The compound as defined in claim 1 which is cis-2-ethoxycarbonyl-1,2,3,4,4a,9b-hexahydro-4a-phenyl-benzofuro[3,2-c]pyridine or a pharmaceutically acceptable salt thereof.

10. The compound as defined in claim 1 which is cis-2-cyclopropylcarbonyl-1,2,3,4,4a,9b-hexahydro-4a-phenyl-benzofuro[3,2-c]pyridine or a pharmaceutically acceptable salt thereof.

11. The compound as defined in claim 1 which is cis-1,2,3,4,4a,9b-hexahydro-4a-phenyl-2-phenylacetyl-benzofuro[3,2-c]pyridine or a pharmaceutically acceptable salt thereof.

12. The compound as defined in claim 1 which is cis-1,2,3,4,4a,9b-hexahydro-2-(3-phenoxypropyl)-4a-phenyl-benzofuro[3,2-c]pyridine or a pharmaceutically acceptable salt thereof.

13. The compound as defined in claim 1 which is cis-2-cyanomethyl-1,2,3,4,4a,9b-hexahydro-4a-phenyl-benzofuro[3,2-c]pyridine or a pharmaceutically acceptable salt thereof.

14. The compound as defined in claim 1 which is cis-2-[3-(4-fluorobenzoyl)-propyl]-1,2,3,4,4a,9b-hexahydro-4a-phenyl-benzofuro[3,2-c]pyridine ethylene ketal or a pharmaceutically acceptable salt thereof.

15. The compound as defined in claim 1 which is cis-2-[3-(4-fluorobenzoyl)-propyl]-1,2,3,4,4a,9b-hexahydro-4a-phenyl-benzofuro[3,2-c]pyridine or a pharmaceutically acceptable salt thereof.

16. The compound as defined in claim 1 which is cis-2-(2-cyanoethyl)-1,2,3,4,4a,9b-hexahydro-4a-phenyl-benzofuro[3,2-c]pyridine or a pharmaceutically acceptable salt thereof.

* * * * *

UNITED STATES PATENT AND TRADEMARK OFFICE
CERTIFICATE OF CORRECTION

PATENT NO. : 4,544,745

DATED : October 1, 1985

INVENTOR(S) : Solomon S. Klioze

It is certified that error appears in the above-identified patent and that said Letters Patent is hereby corrected as shown below:

The chemical structure formula appearing at the top of Column 33, Claim 1, should appear as shown below:

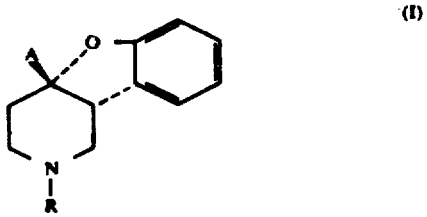

Signed and Sealed this

Eighteenth Day of February 1986

[SEAL]

Attest:

DONALD J. QUIGG

Attesting Officer

Commissioner of Patents and Trademarks